(12) United States Patent
Young et al.

(10) Patent No.: US 9,951,309 B2
(45) Date of Patent: Apr. 24, 2018

(54) STEM CELL PACKAGING AND SHIPPING

(75) Inventors: Wise Young, New Brunswick, NJ (US); Dongming Sun, Princeton Junction, NJ (US); Robert Fleischaker, Carlsbad, CA (US); Kam Sze Kent Tsang, Hong Kong (CN)

(73) Assignee: Stemcyte Inc., Covino, CA (US)

( * ) Notice: Subject to any disclaimer, the term of this patent is extended or adjusted under 35 U.S.C. 154(b) by 615 days.

(21) Appl. No.: 13/985,878

(22) PCT Filed: Feb. 14, 2012

(86) PCT No.: PCT/US2012/025078
§ 371 (c)(1),
(2), (4) Date: Oct. 30, 2013

(87) PCT Pub. No.: WO2012/112572
PCT Pub. Date: Aug. 23, 2012

(65) Prior Publication Data
US 2014/0051165 A1 Feb. 20, 2014

Related U.S. Application Data

(60) Provisional application No. 61/444,207, filed on Feb. 18, 2011.

(51) Int. Cl.
C12N 5/073 (2010.01)
A01N 1/02 (2006.01)
C12M 1/00 (2006.01)

(52) U.S. Cl.
CPC ......... *C12N 5/0605* (2013.01); *A01N 1/0273* (2013.01); *C12M 99/00* (2013.01); *F04C 2270/0421* (2013.01)

(58) Field of Classification Search
CPC .......... C12N 9/88; C12N 1/20; C12N 9/0083; C12N 9/1029; C12N 9/16; C12N 9/2437; C12N 9/93; C12P 5/02; C12P 7/62; C12P 19/02; C12P 19/04; C12P 19/12; C12P 5/023; C12P 5/026; C12P 7/04; C12P 7/10; C12P 7/16; C12P 7/24; C12P 7/26
See application file for complete search history.

(56) References Cited

U.S. PATENT DOCUMENTS

| | | | |
|---|---|---|---|
| 2,702,034 A | 2/1955 | Walter | |
| 4,212,299 A * | 7/1980 | Yokokoji | B32B 27/08 128/DIG. 24 |
| 4,222,379 A | 9/1980 | Smith | |
| 4,714,680 A * | 12/1987 | Civin | A61K 35/28 435/347 |
| 4,721,096 A * | 1/1988 | Naughton | A61K 35/28 128/898 |
| 4,946,437 A * | 8/1990 | Sredni | A61K 31/095 604/20 |
| 5,728,581 A * | 3/1998 | Schwartz | C12M 23/02 435/297.1 |
| 2002/0132343 A1* | 9/2002 | Lum | C12N 5/0647 435/372 |
| 2008/0050347 A1 | 2/2008 | Ichim | |
| 2008/0166324 A9 | 7/2008 | Chow | |

FOREIGN PATENT DOCUMENTS

| | | |
|---|---|---|
| CN | 1120806 A | 4/1996 |
| CN | 101298606 | 11/2008 |
| CN | 101298606 A | 11/2008 |
| EP | 1864641 | 12/2007 |
| EP | 1864641 A1 | 12/2007 |
| JP | 2005287305 | 10/2005 |
| JP | 2005287305 A | 10/2005 |
| WO | 199110726 A1 | 7/1991 |
| WO | 1995017134 A1 | 6/1995 |
| WO | 2010122542 A1 | 10/2010 |
| WO | WO2010122542 | 10/2010 |

OTHER PUBLICATIONS

Thompson, "Flow cytometric analysis of stem cells derived from umbilical cord blood," Univ. of Pretoria (Jan. 22, 2010); Dissertation.
Wagner et al., "Umbilical cord and placental blood hematopoetic stem cells: collection, cryopreservation, and storage," J. hematotherapy (1992); 1(2):167-173.
Hao et al., "Studies on the dynamics of biological characteristics of CD133+ cells from hman umbilical cord blood during short-term culture," (Dec. 2003); 11(6):569-675; Abstract Only.
V. Antonenas et al., "Fresh PBSC harvests, but not BM, show temperature-related loss of CD34 viability during storage and transport" Cytotherapy, vol. 8, No. 2, Jan. 1, 2006, pp. 158-165.
Nikos Tsagias et al., "Time and temperture before processing influence the recovery of umbilical cord blood hematopoietic progenitors", Transfusion, vol. 47, No. 8, Aug. 1, 2007, pp. 1550-1552.
Laluppa J. A. et al., "Culture Materials Affect Ex Vivo Expansion of Hematopoietic Progenitor Cells" Journal of Biomedical Materials Research, vol. 36, Jan. 1, 1997, pp. 347-359.
Anonymous: "Custom Teflon Bags, FED Bags, PFA Films and Extruded FEP Lay Flat Bags, Tubing-American Durafilm", May 5, 2009.
Antonenas et al., "Fresh PBSC harvests, but not BM, show temperature-related loss of CD34 viability during storage and transport," Cytotherpay (2006) 8(2):158-165.
Laluppa et al., "Culture materials affect ex vivo expansion of hematopoietic progenitor cells," Journal of Biomedical Materials Research (Jan. 1, 1997); 36:347-359.
Anonymous: "Custom Teflon Bags, FEP Bags, PFA Films and Extruded FEP Lay Flat Bags, Tubing—American Durafilm," (May 5, 2009); retrieved from the internet: URL: https://web.archive.org/web/20090505205824/http://www.american durafilm.com/teflon_bags_lay_flat_tubing.cfm.
Tsagias et al., "Time and temperature before processing influence the recovery of umbilical cord blood hematopoietic progenitors," Transfusion (Aug. 1, 2007); 47(8):1550-1552.
Berz et al., "Cryopreservation of Hematopoietic Stem Cells," American Journal of Hematology (2007); 82:463-472.

(Continued)

*Primary Examiner* — Blaine Lankford
(74) *Attorney, Agent, or Firm* — Fox Rothschild LLP

(57) ABSTRACT

This invention concerns methods of packaging and shipping stem cells. Also disclosed are related package products.

17 Claims, 15 Drawing Sheets

(56) References Cited

OTHER PUBLICATIONS

Goudar et al., "Decreased pCO2 Accumulation by Eliminating Bicarbonate Addition to High Cell-Density Cultures," Biotechnology and Bioengineering (Apr. 15, 2007); 96(6):1107-1117.
Anon: "Stem Cell Differentiation—Differentiation of mesenchymal stem cells under shear stress in the BioFlux system," Fluxion (2008), pp. 1-2 retrieved from the internet on Mar. 29, 2017: URL:http://www.novelscience.co.jp/img/products/bioflux/1039-1.pdf.

* cited by examiner

IMDM vs. CIM

STEM CELL PACKAGING AND SHIPPING

CROSS REFERENCE TO RELATED APPLICATION

This application is a U.S. National Phase of International Application No. PCT/US2012/025078 filed on Feb. 14, 2012, which claims priority under 35 U.S.C. § 119(e) to U.S. Provisional Patent Application Ser. No. 61/444,207, filed on Feb. 18, 2011. The contents of the applications are incorporated herein by reference in their entirety.

FIELD OF INVENTION

This invention relates to processes and products for packaging and shipping of various stem cells.

BACKGROUND OF INVENTION

Stem cells are types of cells characterized by the ability to renew themselves through mitotic cell division and differentiate into a diverse range of specialized cell types. Human stem cells are typically totipotential or pluripotential precursor cells capable of self renewal and generating a variety of mature human cell lineages. This ability serves as the basis for the cellular differentiation and specialization necessary for organ and tissue development. Recent evidence demonstrates that stem cells can be employed to repopulate many, if not all, tissues and restore physiologic and anatomic functionality. Accordingly, stem cells have the potential to be used in treating a wide variety of diseases and injuries, including nervous system trauma, malignancies, genetic diseases, hemoglobinopathies, and immunodeficiency. Many different types of mammalian stem cells have been characterized. Examples include embryonic stem cells, embryonic germ cells, adult stem cells, and other committed stem cells or progenitor cells are known. In addition, umbilical cord blood is a known alternative source of mesenchymal stem cells as well as hematopoietic stem cells and progenitor cells.

However, applications of these cells are often hampered by logistical issues. For example, stem cells (including cord blood cells), once collected, are routinely cryopreserved at storage facilities (such as cell banks) and, when needed, transported from the facilities to hospitals. This cryopreservation process, where cells or tissues are preserved by cooling to low sub-zero temperatures, typically 77 K or −196° C. (the boiling point of liquid nitrogen), entails certain risks. For example, cells being preserved can be damaged due to freezing during the approach to low temperatures or warming to room temperature. These risks are particularly serious for stem cells (including cord blood cells) as one of the most important aspects in stem cell transplantation is the number of viable stem cells and their developmental potentials at time of transplantation. Out of this concern, stem cells are routinely shipped cryopreserved over a time period as short as possible. Indeed, overnight shipments on dry ice or in a liquid nitrogen shipper are the industry standard and extra care must be taken to monitor the temperatures. Yet, this practice does not eliminate the risks. Also, it is extraordinarily costly and not practical for long-distance (e.g., trans-continental) transportation.

Thus, there is a strong need for more practical processes or methods of shipping stem cells. The present invention satisfies this and other needs.

SUMMARY OF INVENTION

This invention is based, at least in part, on an unexpected discovery that a method for packaging and shipping stem cells does not require cryopreservation and does not significantly compromise stem cells' viability or developmental potentials.

Accordingly, one aspect of this invention features a packaging product that contains a composition containing a plurality of pluripotent cells, and a container comprising a substrate; the substrate has a polymer. The polymer can be polytetrafluoroethylene (PTFE), perfluoroalkoxy (PFA), fluorinated ethylene propylene (FEP), polyvinylidene fluoride (PVDF), polyethylene, or polyvinyl chloride (PVC), which has properties of low friction or non-stickiness. The polymer can also be other polymers suitable for biologicals, such as ultra-low density polyethylene, low-density polyethylene (LDPE), linear low density polyethylene (LLDPE), high density polyethylene (HDPE), coaxially oriented polypropylene (COPP), biaxially oriented polypropylene (BOPP), polyethylene terephthalate (PET), polymide resins such as nylon, ethylene vinyl alcohol polymer (EVOH), and their metalized versions.

The packaging product can be in any suitable shapes, including, but not limited to, a bag, a syringe or a vial for an injector. In one example, the product is pre-filled with stem cells for clinical uses. The pluripotent cells can be stem cells, such as hematopoietic stem cells or mesenchymal stem cells. The composition can contain peripheral blood cells, cord blood cells, or bone marrow cells.

The composition can have a temperature within the range of 5-40° C., such as 5-37° C., 5-30° C., 10-30° C. or 15-25° C. The composition can contain a culture medium, preferably, a $CO_2$ independent medium (CIM). In a preferred embodiment, the medium contains serum, such as human serum of, e.g., 0.5-20% (e.g., 1, 2, 3, 4, 5, 7, 8, 9, 10, 15, and 20%). In another embodiment, the composition is a pharmaceutical composition and contains a pharmaceutically acceptable carrier. The packaging product can be sealed for purposes of, e.g., shipping. The composition can contain at least $1\times10^6$ cells, e.g., $2\times10^6$, $5\times10^6$, $10\times10^6$, $20\times10^6$, $40\times10^6$, $80\times10^6$, $100\times10^6$, or $200\times10^6$ cells. The above-mentioned cells can be $CD34^+$, $CD133^+$, $CD34^+$ $CD133^+$, or other type of stem cells.

In one embodiment, the above-mentioned cells (e.g., peripheral blood cells, cord blood cells, or bone marrow) can be those that have been frozen and thawed, e.g., those obtained from a blood bank. In that case, the medium can contain DNAse (e.g., human DNAse) of about 10-100 U/ml, e.g., 10, 15, 20, 25, 30, 40, 50, 60, 70, 80, 90, or 100 U/ml. Alternatively, the cells can be freshly obtained from a donor and have not been frozen and, in this case, DNAse is not necessary and the composition can be free of DNAse.

In a second aspect, the invention features a method for making the above-mentioned packaging product. The method includes steps of (a) providing a composition containing pluripotent cells; (b) providing a container comprising a substrate, wherein the substrate comprises a polymer; (c) placing the composition in the container; and, (d) sealing the container.

In a third aspect, the invention features a method for shipping stem cells. The method includes steps of providing the above-mentioned packaging product and delivering the packaging product to a recipient, such as a courier, an agent or personnel of a receiving hospital. During the delivering step, the temperature can be within the range of 5-40° C., such as 5-37° C., 5-30° C., 10-30° C., 12-28° C., or 15-25° C. (i.e., room temperature or RT). Using the method, the cells can be delivered over 1-8 days, e.g., at least 24 hours or 2, 3, 4, 5, 6, 7, or 8 days.

Upon the delivering, the pluripotent cells can have a recovery rate of more than 40% (e.g., 45%, 50%, 55%, 60%, 65%, 70%, 75%, 80%, 85%, 90%, and 95%). Also, upon the delivering, the pluripotent cells can have a viability (as determined by the Trypan Blue Exclusion method disclosed herein) of more than 50% (e.g., 45%, 50%, 55%, 60%, 65%, 70%, 75%, 80%, 85%, 90%, and 95%). In one embodiment, upon the delivering, the pluripotent cells can have more than 0.5% $CD34^+$ cells (e.g., 0.55%, 0.6%, 0.65%, 0.7%, 0.75%, 0.8%, 0.85%, 0.9%, 0.95%, 1.0%, 1.1%, 1.15%, 1.2%, 1.3%, 1.4%, 1.5. %, 1.6%, 1.7%, 1.8%, 1.9. %, or 2.0%). In another embodiment, upon the delivering, the pluripotent cells can have more than 0.25% $CD133^+$ cells (e.g., 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.15%, 1.2%, 1.3%, 1.4%, 1.5. %, 1.6%, 1.7%; 1.8%, 1.9. %, or 2.0%). In yet another embodiment, upon the delivering, the pluripotent cells are capable of forming more than 2 (e.g., 5, 10, 15, 20, 25, or 30) $CFU/5 \times 10^4$ cells. The above-mentioned values can be determined according to the methods described in the examples below.

The details of one or more embodiments of the invention are set forth in the description below. Other features, objects, and advantages of the invention will be apparent from the description and from the claims.

DETAILED DESCRIPTION OF THE INVENTION

The present invention relates to packaging and/or shipping stem cells or stem cell-containing preparations (e.g., umbilical cord blood) under conditions such as room temperature (i.e., 15-25° C.) over an extended period. Stem cells and preparations thus packaged and shipped unexpectedly had satisfactory viabilities and development potentials for clinical uses.

Figure 1:
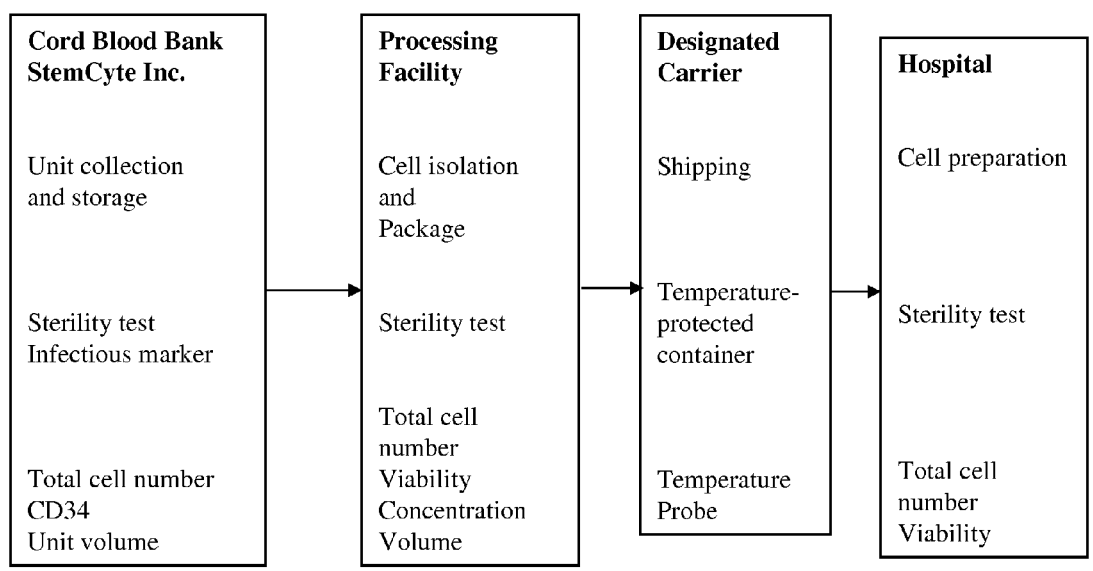
FIG. 1 is a flowchart showing operations in an exemplary procedure of stem cells collection, processing, shipping, and testing upon receipt.

Shown in FIG. 1 is an example of a procedure of collecting, processing, shipping, and testing cord blood cells or a cell component isolated from cord blood.

Briefly, cord blood cells can be collected on site at a hospital or obtained from a cord blood bank (such as that maintained by STEMCYTE Inc.). Although any art-recognized procedures for collecting and storage can be used, a preferred procedure is described in the examples below. Generally, sterility test for various infectious markers should be conducted. In addition, total cell number, CD34+ cell number, and unit volume should be determined and recorded before be freezing for cryopreservation. The collected blood contains red blood cells (RBCs), which tend to break down during freezing and thawing. In that case, once lysed, DNA of RBCs increases viscosity of the collected cord blood cells and hinders further handling of the cord blood cells for clinical uses. To prevent this, DNAse can be added to the collected cells before cryopreservation for breaking down DNA. Doing so can reduce stickiness and clumping of cells and thereby, allow better separation of cells in osmotic gradients (e.g., FICOLL). A number of commercially available DNAses can be used. Examples include PUL-MOZYME® marketed by GENENTECH.

Alternatively, the cord blood can be processed to remove red blood cells so that red blood cell is substantially depleted. If desired, the cord blood can be separated into a number of useful units (e.g., total mononuclear cells (TMN), white blood cells, lymphocytes, CD34+ cells, CD133+ cells, macrophages, and other cells) by osmotic gradients (e.g., FICOLL) or in the manner described in Example 1 below. Also, as mentioned above, the cord blood cells to be shipped can be freshly obtained from a donor and have not been frozen. In these approaches, DNAses are not necessary during packaging and/or shipping such fresh units. Furthermore, plasma can be depleted according to methods known in the art, e.g., those described in US Application 20080166324, the content of which is incorporated by reference in its entity.

Then, the collected cells are packaged and prepared for shipping in a processing facility either on site in the hospital or off site at, e.g., the above-mentioned blood bank. If the cells have been cryopreserved, they can be thawed in the manner described in Example 1 below. Again, sterility test for various infectious markers can be conducted and total cell numbers, CD34+ cell numbers, concentrations, and unit volume should be determined and recorded. Then, the cells are placed in the above-described container to form a package for shipping by a designated carrier.

While a number of media can be used, $CO_2$ independent media (CIM) are preferred. These CIM media prevent potassium depletion and result in better cell survival rate. Also, they are capable of maintaining long term pH stability without atmospheric $CO_2$ (0.04%). Examples of the CIM media include those marketed by GIBCO under, e.g., Cat. No. 8045. Use of human serum is also preferred.

The cells can be used to form a pharmaceutical composition having a pharmaceutically acceptable carrier. As a non-limiting example, normal buffered saline (e.g., about 135-150 mM NaCl) can be employed as the pharmaceutically acceptable carrier. Other suitable carriers include, but are not limited to, water, buffered water, 0.4% saline, 0.3% glycine, and the like. Additional carriers suitable for use in delivering the cultured stem cells and lithium salts of the present invention are described in, e.g., REMINGTON'S PHARMACEUTICAL SCIENCES, Mack Publishing Co., Philadelphia, Pa., 18th ed. (1995).

As disclosed herein, the material of the container is important. In general, the material can be a polymer that is of low friction or non-stickiness to cells, and not toxic to cells or harmful to stem cells recipients. Examples of suitable polymer include, but not limited to, polytetrafluoroethylene (PTFE), perfluoroalkoxy (PFA), fluorinated ethylene propylene (FEP), polyvinylidene fluoride (PVDF), polyethylene, polyvinyl chloride (PVC), ultra-low density polyethylene, low-density polyethylene (LDPE), linear low density polyethylene (LLDPE), high density polyethylene (HDPE), coaxially oriented polypropylene (COPP), biaxially oriented polypropylene (BOPP), polyethylene terephthalate (PET), polyamide resins such as nylon, ethylene vinyl alcohol polymer (EVOH), and their metalized versions. Other polymers can also be used if their coefficients of frictions (against polished steel) are comparable to or lower than those of the above-mentioned polymer. Coefficients of frictions of the above-mentioned polymers are known in the art and incorporated by reference. For examples, coefficients of frictions can be lower than 0.5, such as 0.4, 0.3, 0.2, or 0.1. In preferred embodiment, one can use PTFE, PFA, PEP, or PVDF-based container marketed by DUPONT under the brand TEFLON, HYCLONE'S polyethylene-based containers, or TERUMO's PVC-based containers.

The substrate of the container can be formed into any shapes suitable for receiving and holding cells. Examples of the shapes include, but are not limited to, a bag, a tube, a syringe or a vial for an injector. In some embodiments, the substrate is formed in a shape suitable for culture or for a site of stem cell transplantation or implantation in various tissues, such as CNS. Examples include a tape, a membrane, a thread, a slide, a micro-bead, a micro-particle, a cell culture plate, a multi-well plate, and a bioreactor, all of which can receive cells.

As described herein, during the shipping, the cells in the package do not have to be kept at a lower temperature, e.g., cryopreserved, or delivered overnight. Instead, the cells can be shipped within a rather broader temperature range, including room temperature, over a fairly extended period of time (e.g., 3-8 days). Despite these less stringent conditions, it is preferred that the package is shipped in a temperature-protected container and/or monitored with a temperature probe so as to provide a shipper or recipient with the information if needed. Due to the less stringent conditions, the costs associated with shipping cryopreserved cells are avoided. In addition, as the shipping time can be as long as 5-8 days, long-distance, such as transcontinental, shipping becomes practical. As a result, patients who are far away from a source of particular stem cells (e.g., those having a rare, matched HLA-type) will be able to benefit from stem cell transplantation.

Upon receipt of cells from a courier, the cells can be processed in the manner described in the examples below and tested for their suitability for transplantation. To this end, the following four criteria can be used to determine whether the cells are suitable for transplantation.

Cell Count.

There must be enough viable cells for transplantation and analyses. Preferably, at least twice the number of cells needed for transplantation (e.g., into the spinal cord) are preferred so that there would be enough leftover cells for analyzing the cells. For example, as disclosed in Example 2 below, for Groups A, B, and C, 16, 32, and 64 µl of cell suspensions (100,000 cells/µl) were needed for transplantation. In other words, 1.6, 3.2, and 6.4 million cells were used. Doubling this amount would require a minimum of 3.2, 6.4, and 12.8 million mononuclear cells, respectively. If the shipment contains fewer cells, the shipment should not be suitable for transplantation.

Viability

Too many dead cells should be avoided in the preparation. To this end, manual count using Trypan Blue Exclusion (TBE) can be used as a criterion of viability. Expressed as a percentage, the TBE of the cell suspension represents non-blue-stained cells divided by the total number of stained and unstained cells. For cells designated for transplantation, TBE should be at least 70%. In general, wash procedures as described in the examples below eliminate dead cells and the cell suspensions typically have a TBE greater than 90% just before transplantation.

Contamination

Any evidence or risk of contamination should be reported. This includes, for example, the presence of any leakage of fluids in the shipping bags, abnormal turbidity in the cell suspensions, bacteria or fungi visible under the microscope, or report of previous contamination. As disclosed herein, care should be taken to exclude cord blood units that are positive for maternal hepatitis B core antigen, as well as all other infections agents that would normally exclude a cord blood unit from registration under National Marrow Donor Program (NMDP).

Mononuclear Cells

The final preparation should have 95% or more mononuclear cells. If the viability count of the cells reveals more than 5% other cells, such as red blood cells or neutrophils, the cells will not be used for transplantation. Note that there may be some immature red nucleated cells in umbilical cord blood.

In a preferred embodiment, the package should be rejected if the following is true: (i) the temperature profile shows temperature outside of the designated permissible range of 12° C. to 28° C. and (ii) total time elapses since initial thawing (of the cord blood unit for processing) does not exceed 5 day.

In the above described procedures, antibiotics can be added to a cell preparation. For example, gentamycin can be added at the beginning of cell processing to reduce risk of contamination during processing and shipping. The gentamycin may suppress bacterial growth even though multiple past media fill tests have dictated that contamination was not being introduced. At the recipient hospital, the cells are washed and resuspended twice, markedly diluting antibiotic that may be in the cell suspension. It was found that, during a period of six months, cultures of the wash solutions did not yielded any positive culture in over 15 units of cord blood processed. Likewise, none of the 2-week CFU cultures showed any bacterial growth.

In the above described procedures, the cord blood stem cells can be further treated to expand the pool of stem cells, i.e., in vitro expansion, using methods such as those described in US Applications 20100189696, 20100323920, 20080227197, and 20080166324, the contents of which are incorporated by reference in their entities. The term "in vitro expansion" refers to the cultivation of stem cells in the laboratory. Such cells can be extracted from a mammal and additional quantities of cells generated by cultivation in the appropriate environment, e.g., in media containing a lithium salt. If possible, stable cell lines are established to allow for continued propagation of cells.

Various stem cells can be used to practice this invention. Examples of the stem cells include umbilical cord blood cells, hematopoietic stem cells, embryonic stem cells, bone marrow stem cells, peripheral blood stem cells, placental blood, and other stem cells that can differentiate into functional cells, e.g., neuronal or glial cells. The term "stem cell" refers to any cell that is capable of differentiating into a number of final, differentiated, specialized cell types. Stem cells emanate from all germinal layers (i.e., ectoderm, mesoderm, and endoderm). Typical sources of stem cells include embryos, bone marrow, peripheral blood, umbilical cord blood, placental blood, muscle tissue, and adipose tissue.

Stem cells may be totipotent or pluripotent. Totipotent stem cells typically have the capacity to develop into any cell type. Totipotent stem cells can be both embryonic and non-embryonic in origin. Pluripotent cells are typically cells capable of differentiating into several different, final differentiated cell types. For example, pluripotent stem cells can give rise to cells of the nervous system, skin, liver, kidney, blood, muscle, bone, etc. Examples of pluripotent stem cells include, but are not limited to, cord blood stem cells, neural stem cells, hematopoietic stem cells, adipose-derived stem cells, mesenchymal stem cells, placentally-derived stem cells, exfoliated tooth-derived stem cells, and hair follicle stem cells. In contrast, multipotent or adult stem cells typically give rise to limited types of cells. The term stem cell as used herein includes progenitor cells unless otherwise noted. Unipotent stem cells can produce only one cell type, but have the property of self-renewal which distinguishes them from non-stem cells. These stem cells can originate from various tissue or organ systems, including, but not limited to, blood, nerve, muscle, skin, gut, bone, kidney, liver, pancreas, thymus, and the like. In accordance with the present invention, the stem cell can be derived from an adult or neonatal tissue or organ.

The cells described in this invention can be substantially pure. The term "substantially pure", when used in reference to stem cells or cells derived therefrom (e.g., differentiated cells), means that the specified cells constitute a substantial portion of or the majority of cells in the preparation (i.e., more than 20%, 30%, 40%, 50%, 60%, 70%, 80%, 90%, or 95%). For example, a substantially purified population of cells constitutes at least about 70% of the cells in a preparation, usually about 80% of the cells in a preparation, and particularly at least about 90% of the cells in a preparation (e.g., 95%, 97%, 99% or 100%).

In a preferred embodiment, umbilical cord blood cells are used. These cells can be obtained as described in the example section below or by methods known in the art and then tested by standard techniques. To confirm the differentiation potential of the cells, they can be induced to form, for example, various colony forming units, by methods known in the art. The cells thus confirmed can be further propagated in a non-differentiating medium culture for more than 10, 20, 50, or 100 population doublings without indications of spontaneous differentiation, senescence, morphological changes, increased growth rate, or changes in ability to differentiate into neurons. The cells can be stored by standard methods before use.

The terms "proliferation" and "expansion" as used interchangeably herein with reference to cells, refer to an increase in the number of cells of the same type by division. The term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. Differentiation may be assessed, for example, by monitoring the presence or absence of lineage markers, using immunohistochemistry or other procedures known to a worker skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages. The terms "lineage commitment" and "specification," as used interchangeably herein, refer to the process a stem cell undergoes in which the stem cell gives rise to a progenitor cell committed to forming a particular limited range of differentiated cell types. Committed progenitor cells are often capable of self-renewal or cell division. The term "terminal differentiation" refers to the final differentiation of a cell into a mature, fully differentiated cell. For example, hematopoietic progenitor cells and muscle progenitor cells can differentiate into neural or glial cell lineages, terminal differentiation of which leads to mature neurons or glial cells. Usually, terminal differentiation is associated with withdrawal from the cell cycle and cessation of proliferation.

The term "progenitor cell," as used herein, refers to a cell that is committed to a particular cell lineage and which gives rise to cells of this lineage by a series of cell divisions. Examples of progenitor cells include precursor cells for the neuronal, hepatic, nephrogenic, adipogenic, osteoblastic, osteoclastic, alveolar, cardiac, intestinal, or endothelial lineage.

The term "culturing" refers to maintaining stem cells under conditions in which they can proliferate and avoid senescence. For example, in the present invention, stem cells are cultured in media containing a lithium salt and optionally one or more growth factors, i.e., a growth factor cocktail.

The term "umbilical cord blood" refers to a source of pluripotent and multipotent stem cells obtained from the blood of umbilical cords that are left over after birth. Examples of stem cells found in umbilical cord blood include, but are not limited to, mesenchymal stem cells, hematopoietic stem cells, and progenitor cells. Mesenchymal stem cells and progenitor cells can typically differentiate into nerve cells, marrow stromal cells, chondrocytes, osteoblasts, adipocytes, myocytes, tenocytes, and ligament cells. Hematopoietic stem cells can typically give rise to cells of the lymphoid, myeloid, and erythroid lineages. A detailed description of methods for collecting and processing cord blood is provided below.

The term "umbilical cord blood unit" refers to a volume of cord blood that is collected from a single donor. A single umbilical cord blood unit is typically used in the methods of the present invention, but multiple cord blood units, e.g., double cord blood units, can also be used to increase stem cell number.

As used herein, the terms "plasma is substantially depleted" and "plasma-depleted" refer to processed umbilical cord blood units in which a volume of plasma greater than about 30%, 35%, 40%, 45%, 50%, 55%, 60%, 65%, 70%, 75%, 80%, 85%, 90%, or 95% has been removed. For example, plasma can be substantially depleted by centrifuging cord blood and separating the cellular fraction from the plasma fraction. The plasma volume remaining following substantial depletion is typically from about 0% to about 30% by volume, preferably from about 10% to about 30% by volume.

The terms "non-red blood cell-depleted" and "red blood cells are not depleted" as used herein refer to processed umbilical cord blood units in which a volume of red blood cells less than about 30%, 25,%, 20%, 15%, 10%, 5%, 4%, 3%, 2%, or 1% has been removed. As used herein, the terms "red blood cell is substantially depleted" and "red blood cell-depleted" refer to processed umbilical cord blood units in which a volume of red blood cells greater than about 30%, 35%, 40%, 45%, 50%, 55%, 60%, 65%, 70%, 75%, 80%, 85%, 90%, or 95% has been removed.

"Nucleated cells" refers to cells that have a nucleus, i.e., an organelle that comprises chromosomal DNA. Nucleated cells include, e.g., white blood cells and stem cells. "Unnucleated cells" includes, e.g., adult red blood cells.

Example 1

This example describes an exemplary procedure for controlled thawing of frozen single-bag STEMCYTE Umbilical Cord Blood Units (UCBU) and packaging.

I. Preparation of Hsa/Gentran Wash

The following items were placed in a Biological Safety Cabinet (BSC): 4 alcohol wipes, 1 thawing Bag Set (Transfer Pack Unit), 1 bag Gentran 40, 1 syringe filter, 1 (2)×50 mL HAS, 1 needle, 1 plasma transfer set, and 1 scissor. Inside the Biological Safety cabinet, the outer injection port of bag #1 of the thawing bag set was spiked with one end of a plasma transfer set. If the unit was less than or equal to 100 mL cryopreserved volume, a 300 mL transfer set was used; if unit was greater than 100 mL, a 600 mL transfer set was used. The cap was then removed and the rubber diaphragm of a 50 mL vial of HSA was cleaned with a 70% Isopropyl Alcohol (IPA) wipe. The HSA diaphragm was spiked with the second spike of the plasma transfer set mentioned above. A hypodermic needle, with syringe filter attached, was inserted into the HSA diaphragm next to the plasma spike, to vent the vial. The HSA vial was raised above bag #1 to allow the entire contents of the vial (50 mL) to flow into the transfer bag. For UCBU with volumes >100 mL, 2 vials (100 mL) should be drained into a 600 mL transfer bag. The tubing between the HSA vial and bag #1 was heat sealed near the injection port of bag #1 before discarding the HSA vial and excess tubing. The remaining injection port of bag #1 was spiked with a new plasma transfer set before closing the roller clamp on transfer set tubing. The injection port of the Gentran 40 bag was spiked with the other end of the plasma transfer set.

Then, bag #1 was placed on the electronic scale and tare to zero. Transfer tubing was unclamped to allow 190 g of Gentran 40 to run into bag #1 for a UCBU with cryopreserved volume of no greater than 100 mL. When UCBU volume was greater than 100 mL, 380 g of Gentran 40 was transferred into bag #1. The plasma transfer tubing was Heat sealed near bag #1 and discard tubing. The final volume in bag #1 should be approximately 240 mL (or 480 mL) with final concentrations of 5% for HAS and 8% for Gentran. The date, time and operators initials of wash preparation on the label of bag #1 were then recorded. The thawing bag set was placed into a 2°-8° C. refrigerator for approximately 30 minutes prior to thawing the UCBU. The wash solution should be used within 1 day of preparation.

A bag of frozen UCBCs was thawed according to the procedure described below in section II:

II. Thawing/Washing Frozen UCBU

II.1. Place the following items in a BSC before the procedure: 6 (12)×50 mL centrifuge tubes; large, small chilled cold packs; 5 (10)×2.5 mL ampules DNAse; 1000 mL DNAse wash buffer; 100 mL of 250 mM $MgCl_2$; non-particulating wipes; WFI water; 4 (8)×25 gauge needle; 25 mL pipets; sampling site coupler; 2×10 mL syringe; 2×1 mL syringe; IPA wipes; an electronic scale; Hemostats; and a tubing sealer.

2. Calculate volumes of DNAse and 250 mM $MgCl_2$ solution required according to the following formulae: and place the solutions thus prepared in appropriate size syringes with 0.2 mm disc filters and needles for injection.

Volume of DNAse required for HSA/GENTRAN wash=Volume HSA/Gentran wash÷25;

Volume of DNAse required for injection to UCBU bag=Volume UCBU bag÷25;

Volume of 250 mM $MgCl_2$ required for HSA/GENTRAN wash=Volume HSA/Gentran wash÷100;

Volume 250 mM $MgCl_2$ required for injection to UCBU bag=Volume UCBU bag÷100.

II. 3. Pre-chill the refrigerated centrifuge to 2°-8° C.
Centrifuge Settings:
Set the centrifuge speed to 1,860 g's (3,080 rpm on SORVALL HS-4 aluminum rotor with 4-place carrier).
Place the brake on a medium setting. (set deceleration at 7 for HERAEUS SUPERFUGE).

II.4 From the accompanying paper work record the cryopreserved volume.

II.5 Calculate 1.5 volume of the Umbilical Cord Blood Unit (UCBU).

Volume of 1.5 UCBU=Volume UCBU (Step 4 above)×1.5

II.6 Verify HSA/Gentran wash and DNAse wash solutions have been refrigerated at least 30 minutes and not more than 1 day.

II.7 Obtain a plastic bag, approximately 8"×10". Place upright inside a bucket with ice or frozen ice packs. Fill with water to approximately 6-8 inches.

II.8 Put the ice container in the location of the thawing procedure.

II.9 Remove thawing bag set from the refrigerator to BSC. Insert a sampling site coupler into one of the 2 ports and inject DNAse reagent and $MgCl_2$ required for HSA/Gentran wash. Mix and place between cold packs.

II.10 Obtain the frozen UCBU from storage. Verify that the UCBU ID label on cassette matches the required paperwork and record UCBU ID.

II.11 Carefully open the frozen cassette and verify that the UCBU ID number on UCBU bag matches the ID on the cassette and the required paperwork.

II.12 Place the UCBU bag from the cassette into a 8"×10" sterile bag. Place bag containing UCBU into the ice bath. DO NOT submerge ports. Use a timer and time for 5 minutes.

II.13 After 5 minutes, check the UCBU to see if thawed. If not, continue periodic checks until "slushy". Remove the thawed UCBU freezing bag from the ice bath, dry with lint free wipes.
NOTE: Begin following steps for washing immediately.

II.14 Place the UCBU between cold packs inside the BSC, with ports exposed. Gently rock UCBU for 10 seconds to mix.

II.15 Remove the stopper from 1 of the 2 ports on UCBU bag. Spike port with a sampling site coupler.

II.17 Immediately after spiking UCBU port, inject DNAse reagent and $MgCl_2$ for injection into UCBU bag (see step 2 above). Mix gently.

II.18 Spike the remaining port with a spike attached to thawing bag set.
NOTE: Check to be sure that all roller clamps on thaw set tubing are closed before spiking the UCBU.

II.19 Place a cold pack onto a scale. Place the UCBU bag onto the cold pack. Place another cold pack on top of UCBU bag and tare the scale.

NOTE: The UCBU and all materials must be kept at 2°-8° C.

II.20 Clamp a hemostat onto tubing from bag #1. Open the roller clamp on the tubing to the UCBU bag. Unclamp the hemostat on bag #1, to transfer wash solution 1.5 times the volume of UCBU (see step 5 above). Record volume added.

II.21 Upon completion of the wash transfer, clamp the tubing.

NOTE: This initial dilution step should be completed as quickly as possible after thawing.

II.22 Thoroughly mix the wash solution and cord blood in the UCBU bag by rotating the bag manually for approximately 10 seconds, keeping the UCBU between cold packs.

II.23 Remove the aluminum clip, or open the roller clamp if provided, on the tubing near bag #2 and allow the wash/blood mixture to flow into bag #2. Remove as much of the mixture from the UCBU bag as possible. Keep bag #2 between the cold packs during this step.

II.24 Close the tubing near bag #2 once the transfer has completed.

II.25 Place the UCBU bag back between the cold packs resting on the scale platform and tare the scale to zero.

II.26 Unclamp the hemostat near bag #1 and allow additional wash solution equal to the cryopreserved volume of UCBU to flow into the UCBU bag. Reclamp the tubing near bag #1 when complete. Record volume added.

II.27 Close the roller clamp next to UCBU bag that has been washed.

II.28 Thoroughly mix the wash/blood mixture in the UCBU bag. Remove as much of the cord blood as possible from the port/tail areas of the UCBU bag.

II.29 Unclamp the tubing next to bag #2 and allow the wash/blood mixture to flow into bag #2. Roll up the UCBU bag to ensure that as much of the blood as possible is removed from the UCBU bag.

NOTE: At this point, the thawed UCBU has been diluted by wash solution equal to 2.5 times the volume of the cryopreserved UCBU (1.5× initial+ 1.0× additional).

II.30 Clamp the tubing next to bag #2 and close roller clamp next to UCBU bag.

II.31 Heat-seal the tubing immediately, below the "Y" connection leading to the two spikes, but above the clamp next to bag #2. Once sealed, excess tubing may be removed.

II.32 Aseptically spike a port of bag #2 with a new plasma transfer set and transfer the contents of bag #2 to 50 mL tubes kept on ice.

II.33 Balance the centrifuge bucket containing the 50 mL tubes.

II.34 Centrifuge the 50 mL tubes at approximately 1860 g's (3,080 rpm on Sorvall HS-4 aluminum rotor with 4-place carrier) for 15 minutes at 0° C. to 8° C. The centrifuge brake should be set on a medium setting.

II.35 Upon completion of the centrifugation, carefully remove the centrifuged 50 mL tubes. Do not disturb the pellet.

II.36 In the safety cabinet, open centrifuged tubes and aspirate most of the wash leaving approximately 5 mL in the bottom of tube, without disturbing the pellet.

II.37 Add 5 mL of washing buffer and mix gently using a 10 mL pipette.

II.38 Fill the 50 mL tube with washing buffer to the 50 mL mark.

II.39 Centrifuge the 50 mL tubes at approximately 1860 g's (3,080 rpm on Sorvall HS-4 aluminum rotor with 4-place carrier) for 10 minutes at 0° C. to 8° C. The centrifuge brake should be set on a medium setting.

II.40 Upon completion of centrifugation, carefully remove the 50 mL tubes.

II.41 In the safety cabinet, open centrifuged tubes and aspirate most of the wash, leaving approximately 5 mL in the bottom of tube, without disturbing the pellet.

II.42 Re-suspend the cell pellet in each tube by tapping the tubes against the BSC surface.

The thawed UCBCs were then subjected either to blood lysate procedure as described below in section III or to isolation of mononuclear cells (MNC) as described below in section IV.

III. Red Blood Lysate Procedure

III.1 Place the following items in the BSC
6 (12)×50 mL centrifuge tubes
160 mL USP water (Ambient temperature)
160 mL 2× Saline III.2 Add 22.5 mL of ambient temperature USP water to each 50 mL tube. Begin 30 second timer at the end of the addition of water. Mix by pipetting.

III.3 Immediately after 30 seconds, add 22.5 mL of 1.8% (2×) NaCl Solution to the 50 mL tube and mix gently by inverting. Complete Steps III.2 and III.3 individually with each tube.

III.4 Divide each tube into 2 tubes and fill each with washing buffer to 50 mL.

III.5 Centrifuge the 50 ml tubes at approximately 830 g's (2,050 rpm on Sorvall HS-4 aluminum rotor with 4-place carrier) for 10 minutes at 0° C. to 8° C. The centrifuge brake should be set on medium setting.

III.6 Upon completion of the centrifugation, carefully remove the centrifuged 50 mL tubes from the bucket.

III.7 In the safety cabinet, open the centrifuged tubes and aspirate most of the wash leaving approximately 1 mL in the bottom of the tube without disturbing the pellet.

III.8 Add 5 mL of wash buffer and re-suspend the cell pellet gently using 10 ml pipette.

III.9 Wash tubes with additional 10 ml of DNAse wash buffer and pool the cells together into one tube.

III.10 Bring volume of pooled cells to 30 mL with DNAse wash buffer.

NOTE: Begin centrifuge warming by setting temperature to 25° C. and speed to 7,000 rpm. Press start (typically takes ~30').

IV. Isolation of MNCs from Human Umbilical Cord Blood

IV.1 Place the following items in the BSC: 6×50 mL centrifuge tubes; 90 mL LSM; 10×25 mL Pipets; 2×10 mL Pipets; 1 conical tube (225 mL)

IV.2 Dilute the cord blood cells with DNAse wash buffer 1:5 in a 225 mL sterile conical tube. Mix the diluted blood gently by swirling.

IV.3 Place six (6) 50 mL centrifuge tubes in the BSC.

IV.4 Using a sterile 25 mL pipette, dispense 30 mL of the diluted blood into each 50 mL tube.

IV.5 Fill a sterile 10 mL pipette with 13 mL of LSM. Slowly slide pipette down the side of tube to the bottom. Hold the tube at an angle while gently pipetting the LSM below the level of the blood. Slowly remove the pipette against the tube wall to prevent mixing of layers.

NOTE: Do not fully expel the LSM from the pipette— air bubbles will disturb the LSM layer IV.6 Close the tubes and transfer with care to the centrifuge.

IV.7 Place the tubes in the swinging bucket rotor at approximately 467 g's (1,540 rpm on Sorvall HS-4 aluminum rotor with 4-place carrier, or 1600 rpm for S4 180 rotor) for 32 minutes at temperature: 24° C., with brake off (set deceleration at 2 for Heraeus Superfuge). Verify the centrifuge has reached specified speed.

IV.8 Place six (6) sterile 50 NIL tubes in rack in the BSC.

11.9 After centrifugation, remove the tubes carefully from the centrifuge to prevent mixing of the layers, and place in rack with new tubes.

11.10 Set the centrifuge(s) for cooling: Set the temperature to 10° C., and timer 10 minutes. Start the centrifuge by pressing the start key 11.11 Open the centrifuged tubes in the BSC. Aspirate the supernatant, exposing the mononuclear layer. Collect the mononuclear layer (buffy coat) only, using a sterile 10 mL pipette. Transfer to a new tube and fill each tube with DNAse wash buffer to 45 mL.

IV.12 Place the tubes in the swinging bucket rotor(s) and set centrifuge at approximately 467 g's (1,540 rpm on SORVALL HS-4 aluminum rotor with 4-place carrier) for 10 minutes at 10° C. temp, with brake on. medium setting (set deceleration at 7 for HERAEUS SUPERFUGE).

IV.13 After centrifugation, in the safety cabinet, open the tubes and aspirate most of the supernatant, leaving approximately 1 mL, without disturbing the pellet.

IV.14 Label one new 50 mL centrifuge tube: "Pooled MNC," "V90195," "Step IV.14," the lot number of this Manufacturing Direction, today's date, and operator's initials.

IV.15 Re-suspend the cell pellets with 5 mL DNAse wash buffer gently, using a sterile 10 mL pipette. Pool the cells into a single centrifuge tube.

IV.16 After pooling the cells, wash all 6 tubes with 4 mL volume of DNAse wash buffer to ensure all Mononuclear cells (MNC) are collected.

IV.17 Transfer the wash to the labeled "Pooled MNC" tube and add DNAse wash buffer up to 50 mL.

IV.18 Place the tube in the swinging bucket rotor with balance tube, set centrifuge at approximately 467 g's (1,540 rpm on SORVALL HS-4 aluminum rotor with 4-place carrier) for 10 minutes at 10° C. temp, with brake on.

IV.19 After centrifugation, in the safety cabinet, open the tubes and aspirate most of the wash, leaving approximately 1 mL in tube, without disturbing the cell pellet.

IV.20 Re-suspend the pellet with 5 mL of washing buffer, using a sterile 10 mL pipet.

IV.21 Bring the volume of the Pooled MNC tube to 20 mL, mix well.

11.22 Transfer an adequate volume sample of the well-mixed MNC into a tube, for viability and MNC cell count. Record amount sampled.

IV.23 Determine the cell density and % viability.

IV.24 Calculate total number of cells according to formula below:

Viable Cell Density from $IV.23\times(20-\text{amount sampled from } IV.22)$.

IV.25 If the total number of viable cells is less than 20 million, contact a clinical coordinator. Rejected lots are retained pending outcome of investigation.

The cells prepared according to the above-described procedures were then transferred to various transportation bags according to the procedures described in section V below. The following three types of sample bags with luer lok fittings were used: HYCLONE PE sample bags (THERMO SCIENTIFIC), TEFLON® Bags (DU PONT), and TERUFKEX® Transfer bags (TERUMO, PVC).

The HYCLONE PE sample bags (e.g., HYCLONE 60 mL to 20 L 2-D Labtainer with two end ports, such as SH3b6500 and SH3b6500,) were constructed of CX3-9 film, a three layer, 9 mil cast film, where the outer film layer was a polyester elastomer coextruded with an ultra-low density polyethylene contact layer. The TERUFKEX® Transfer bags (e.g., 1BB*T015CB70, 1BB*T030CB71, 1BB*T060CB71, 1BB*T080BB71, 1BB*T100BB71, and 1BB*T200BB71,) were PVC based. TEFLON® Bags were PFA-based (e.g., the PFA Bags −2.0 mil or −5.0 mil TEFLON® Bags).

V. Transfer Cells to Transportation Bags

V.1 Place the following items in the BSC: 2×50 mL centrifuge tubes; 100 mL transportation media (V90199: CIM plus 10% HS, 2 mM GlutaMAX, Galactose and 100 U/mL Gentamicin); and 2×5 mL Pipets; sterile transportation bags:

V.2 Calculate volume transportation media required: Volume transportation media required (mL)=Total number of cells from Step IV.24×10$^{-6}$.

V.3 Place the labeled MNC tube in the swinging bucket rotor with balance tube, set centrifuge at approximately 467 g's (1,040 rpm on Sorvall HS-4 aluminum rotor with 4-place carrier) for 10 minutes at 10° C. temp and brake on medium setting (set deceleration at 7 for Heraeus Superfuge).

V.4 After centrifugation, in the safety cabinet, open the tubes and aspirate the supernatant to the waste container.

V5. Re-suspend the pellet with 5 mL of transportation medium using a sterile 10 mL pipette.

V.6 Add medium to adjust the cell concentration to 1×10$^6$/ml.

V.7 Calculate volume gentamicin required.

Volume gentamicin required (mL)=Total volume of cells from Step $V.2.\div 500$.

V.8 Withdraw 3 ml of cells for retains and transfer to 15 ml conical tube.

V.9 Add gentamicin (volume calculated in V.7) to the cell suspension and mix gently.

V.10 Transfer the cells suspension to a transportation bag.

V.11 Label the bag "MNC PREPARED FROM FROZEN UCBU," an ID#, "V90195," "Step V.11," the lot number of this Manufacturing Direction, the total cell count, today's date, and operator's initials.

V.12 Package cells according to SOP400.014 for transport. Include with the unit of cells a Certificate with product specifications: Unit number, Lot number, Cell count, Viability and Sterility information. Attach copy of COA to this document.

V.13 0.5 mL of cell retain is used to inoculate one tube of TSB broth and 0.5 ml is used to inoculate one tube of Thioglycolate broth.

V.14 1.0 mL of sample is to be stored at 2-8° C. as a retention sample for a period of one week. Label tube with "2-8° C. Retention Sample of MNC PREPARED FROM FROZEN UCBU," an ID number, "Step V.14," the lot number, the total cell count, date, and operator's initials.

V.15 1.0 mL of sample is to be stored at −80° C. as a retention sample. Label the tube with "−80° C. Retention Sample of MNC PREPARED FROM FROZEN UCBU," an ID number, "Step V.15," the lot number, the total cell count, date, and operator's initials.

The cells were packaged in several different media in the manner described above and then transported at a number of different temperatures to a different site over a period of 1-8 days.

Example 2

In this example, assays were conducted to examine cord blood cells packaged and shipped in the manner described in Example 1 above.

Upon arrival of the package of the bags by airfreight, the package was stored in its container in a safe place until processing and the temperature monitor was kept with the package. Before processing, the package was inspected and documented for any change in the package. The total elapsed time since initial thawing of the original unit of blood for processing was also noted.

Unpacking

The shipping container was opened; the package containing hUCB-MNC bags were taken out and kept at the designated temperature (RT). In a biological safety cabinet (BSC), the bags were inspected for damage or leakage. In the biological safety cabinet, the bags were rocked gently to mix the cells. Using a pair of sterile gloves and a luer lock syringe, the contents of each bag were transfer into a sterile 30-, 50-, or 100-ml centrifuge tube labeled as hUCB-MNC. The tubes were then centrifuged at 400×g for 10 minutes at designated temperature (RT). Using the 10 ml pipette, the supernatant from the centrifuge tube was aspirated without disturbing the pellet and saved for sterility test (Sample 1). The cells pellet was resuspended with 1 ml of 1% normal serum albumin (NSA) in clinically graded physiologic saline to form an initial cell suspension for injection.

Viability Assay and Cell Count of the UCB-MNC

1. Viability Assay

In the safety cabinet, 1:10 cell dilution was prepared by using a 100 µl tip to dispense and mix 50 µl of the cell suspension into a 12×75 mm tube containing 450 µl of normal saline supplemented with 1% NSA: Using a 100 µl tip, 40 µl of diluted cell suspension was pipetted to 10 µl of trypan blue solution in a 0.5 ml EPPENDORF tube. After mixing by pipetting several times, the trypan blue-stained cell suspension was charged into an Improved Neubauer counting hemocytometer for counting the numbers of bluish stained dead cells and unstained live cells in four big squares each of 1 mm×1 mm containing 16 small squares. Anucleated RBC could be easily distinguished from unstained viable nucleated cells as they looked like reflecting mirrors under the microscope by focusing the objective up and down. Then, the percentage of viable cells was calculated by dividing the number of unstained cells with the total number of bluish stained and unstained cells.

2. Manual Count

In the safety cabinet, a 1:100 cell dilution was prepared by transferring 50 µl of the above-mentioned initial cell suspension to 450 µl of 3% acetic acid solution with methylene blue in a 12×75 mm tube. The resulting cell suspension was charged into both upper and lower chambers of an Improved Neubauer counting hemocytometer for counting the numbers of bluish stained cells in eight big squares each of 1 mm×1 mm in both upper and lower chambers. The cell number was calculated by dividing the total count by eight and multiplying 100 (dilution factor) and 10,000.

Lysis of RBC by 3% acetic acid was instantaneous, whereas nucleated cells remained intact for at least 40 minutes. Nucleated cells were stained blue in 3% acetic acid supplemented with methylene blue. The cell concentration was optimally adjusted to yield a cell density of approximately 50 in each square of 1 mm×1 mm. The counts derived from the upper ($N_1$) and lower ($N_2$) chambers were comparable in a way that $N_2$ ought to be within the range of $N_1 \pm \sqrt{N_1}$. Otherwise, filling procedure and counting were repeated to avoid non-randomness and imprecision caused by technical imperfection and incompetency.

3. Automated Count

Cell suspension was also counted with the hematology analyzer Beckman Coulter ACT Diff to counter-check the accuracy of manual count.

Cell Preparation

After the cell viability and cell counts were recorded, the cell-containing tubes were centrifuged at 400×g for 5 minutes. The supernatant in each tube was aspirated without disturbing the cell pellet, and the cells were resuspended and adjusted to a concentration of $1 \times 10^5$ viable cells/µl with clinically graded physiologic saline supplemented with 1% NSA. The, 100 µl of the resulting cell suspension was transferred into two sterile 0.25 ml EPPENDORF tubes (one for backup). The cell suspension was then used for the following injection dosages:

a. 4 µl×4 injections ($16 \times 10^5$ viable cells)
b. 8 µl×4 injections ($32 \times 10^5$ viable cells)
c. 16 µl×4 injections ($64 \times 10^5$ viable cells).

Briefly, the EPPENDORF tubes with cells were transported to an operating room. In the operating room, the cell suspension was filled into Hamilton syringes and butterfly needles with clinically graded physiologic saline supplemented with 1% NSA. More specifically, an appropriate volume of cell suspension was filled into 50 µl or 100 µl Hamilton syringes through butterfly needles before being administered to three groups of subjects, A, B, and C. For Group A or B, a 50 µl Hamilton syringe was used to aspirate 20 µl (5 µl×4) for Group A or 40 µl (10 µl×4) for Group B. For Group C, 100 µl Hamilton syringes were used to aspirate 80 µl. Four injections were made into in the dorsal root entry zones of the spinal cord of each subject.

The above-mentioned backup tube was centrifuged at 400×g for 5 minutes. The resulting supernatant was aspirated and saved for sterility test (Sample 2). The cells were then subjected to lineage analysis by direct immunofluorescence (see below) and Colony Forming Unit (CFU) assay.

Sterility Tests

Both above-mentioned Sample 1 and Sample 2 (Step 38) were subject to a sterility test immediately following the hospital's standard protocol or the proper manual protocol Colony Forming Unit (CFU) Assay The number of viable cells was first counted and then cultured to determine the number of CFU formed over 2-week period. Briefly, the cells were pipetted into pre-mixed methylcellulose medium (Methocult H4230; STEMCELL TECHNOLOGIES Inc.) supplemented with growth factors, rhG-CSF, and rhIL-3 in IMDM (Iscove's Modified Dulbecco's Medium). The final adjusted concentrations were 1% methylcellulose, 30% fetal bovine serum, 1% bovine serum albumin, 10-4 M 2-mercaptoethanol, 2 mM 1-glutamine, 10 ng/ml rhIL-3, and 500 ng/ml rhG-CSF. The cells were gently vortexed and 1.1 ml of the cell suspensions ($5 \times 10^4$ cells) were plated in duplicate on 35 mm×10 mmsterile culture dishes (FISHER SCIENTIFIC). After culturing the cells at 37° C. in water saturated 5% $CO_2$ incubator, CFU-GM colonies consisting of 20 or more cells were counted manually with a standard inverted microscope. Cultures contaminated with bacteria or fungus, if any, were noted.

Direct Immunofluorescence Analysis of hUCB-MNC

The following is an optional analysis to be carried out when there were enough leftover cells. Depending on institutional practice, the analytical technique could be either dual or single platform, with or without wash. The ISHAGE gating strategy was used to enumerate $CD34^+$ cells and $CD133^+$ cells.

Reagents required for this analysis included monoclonal antibodies to human cell surface antigens (IgG-PE, CD45-FITC, CD34-PE and CD133-PE), 7-amino-actinomycin (7-AAD; eBioScience or equivalent), ImmunoPrep Whole Blood Lysing Reagents (BECKMAN COULTER), Washing buffer (PBS supplemented with 0.1% sodium azide), Staining buffer (PBS supplemented with 0.1% sodium azide and 1% NSA), 1% paraformaldehyde solution, and 12×75 mm polystyrene test tubes. Below is the staining procedure 1. Adjust nucleated cell count to $<1\times10^7$/ml with 1% NSA, if necessary, from cell suspension prepared at Step 7 of viability assay.
2. Label 12×75 mm tubes, dispense antibodies and cells as follow:

| Antibody      | Tube 1 | Tube 2 | Tube 3 |
|---------------|--------|--------|--------|
| CD45-FITC (μl)| 20     | 20     | 20     |
| CD34-PE (μl)  | —      | 20     | —      |
| CD133-PE (μl) | —      | —      | 10     |
| IgG1-PE (μl)  | 20     | —      | —      |
| 7-AAD (μl)    | 5      | 5      | 5      |
| Cell Sample (μL) | 100 | 100    | 100    |

3. Vortex gently and stand in the dark at 4° C. for 20 minutes or at room temperature for 30 minutes.
4. Lyse, neutralise and fix staining using Q-Prep Dispenser and ImmunoPrep Whole Blood Lysing Reagents. Stand in the dark for at least 1 hour before signal acquisition, or
4a. Add 500 μl of RBC lysis buffer to the cell suspension, mix gently and incubate in the dark for 10 minutes at room temperature. Wash twice with 2 ml of cold wash buffer. Centrifuge at 300×g for 5 minutes at 2-8° C. Remove the supernatant, re-suspend cells in 0.5 ml of 1% paraformaldehyde solution.
5. Acquire no less than 75,000 $CD45^+$ events and a minimum of 100 $CD34^+$ events using ISHAGE protocol as depicted in Figure X1.

Figure 6:
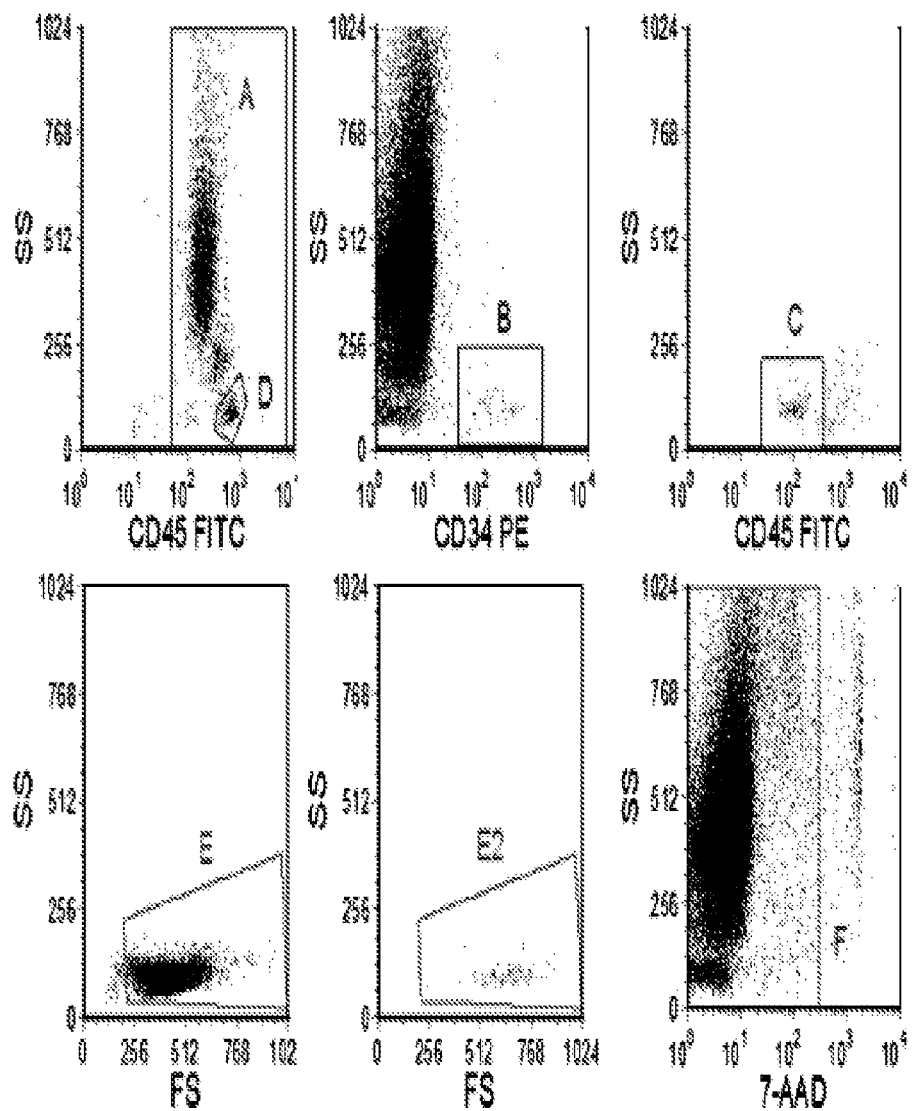
FIG. 6 is set of histograms showing enumeration of $CD34^+$ cells in peripheral blood.
Figure 7:
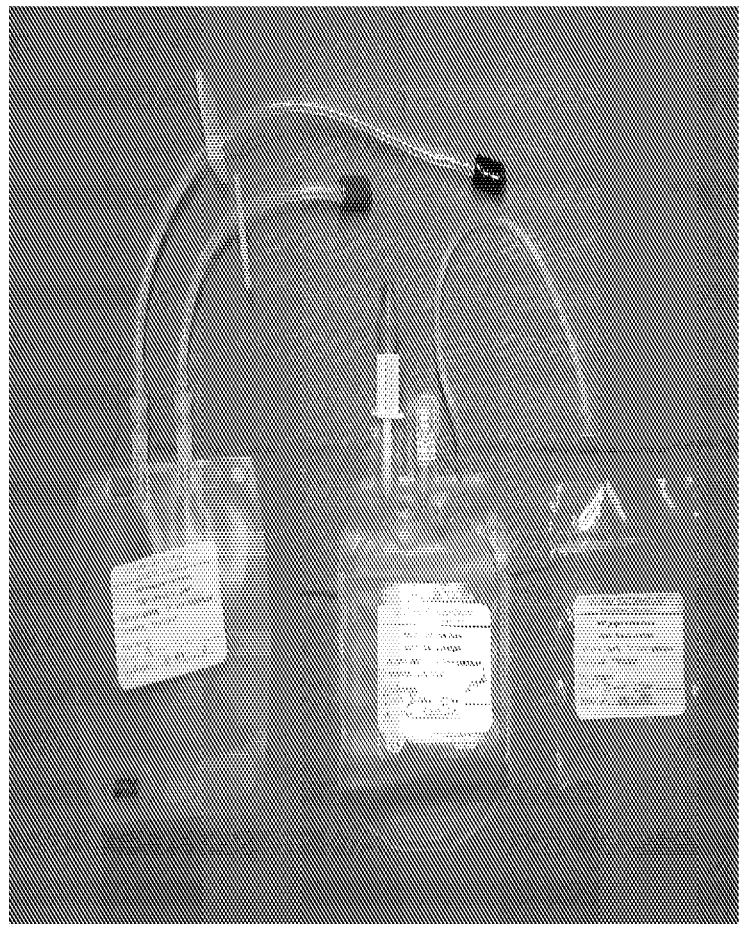

Shown in FIG. 6 is an example of CD34 enumeration using a protocol following the ISHAGE guidelines. Cells were labeled using a no-wash protocol with CD45-FITC and CD34-PE. Before analysis, 7-AAD was added. Region A, was set on a cytogram of SS versus CD45 to delineate the leucocytes. Region B was set to enclose the CD34+ve cells. Region C to include the weakly positive CD45 cells was set on a dot plot of SS versus CD45 gated on (A AND B). Region D was drawn around the lymphocytes on the SS versus CD45 plot and used to gate a plot of SS versus FS. Region E was drawn to include all the lymphocytes and this region was copied onto another scatter plot gated on (A AND B AND C), (E2). Region F was drawn on a dot plot of SS versus 7-AAD to exclude the 7-AAD positive cells (dead) and all the previous plots gated on this region. The cells in region E2 were then recorded as the CD34+ cells.

1. Bag Types and Temperatures

As shown in FIG. 2, when the stem cells were shipped in the above-mentioned three types of bags over a period of 3 days, both the bag types and the shipping temperatures affected the recovery rate (FIG. 2A), cell viability (FIG. 2B), the level of $CD 34^+$ cell population (FIG. 2C), the level of $CD 133^+$ cell population (FIG. 2D), and CFUs (FIG. 1E) to different degrees.

Figure 2A:
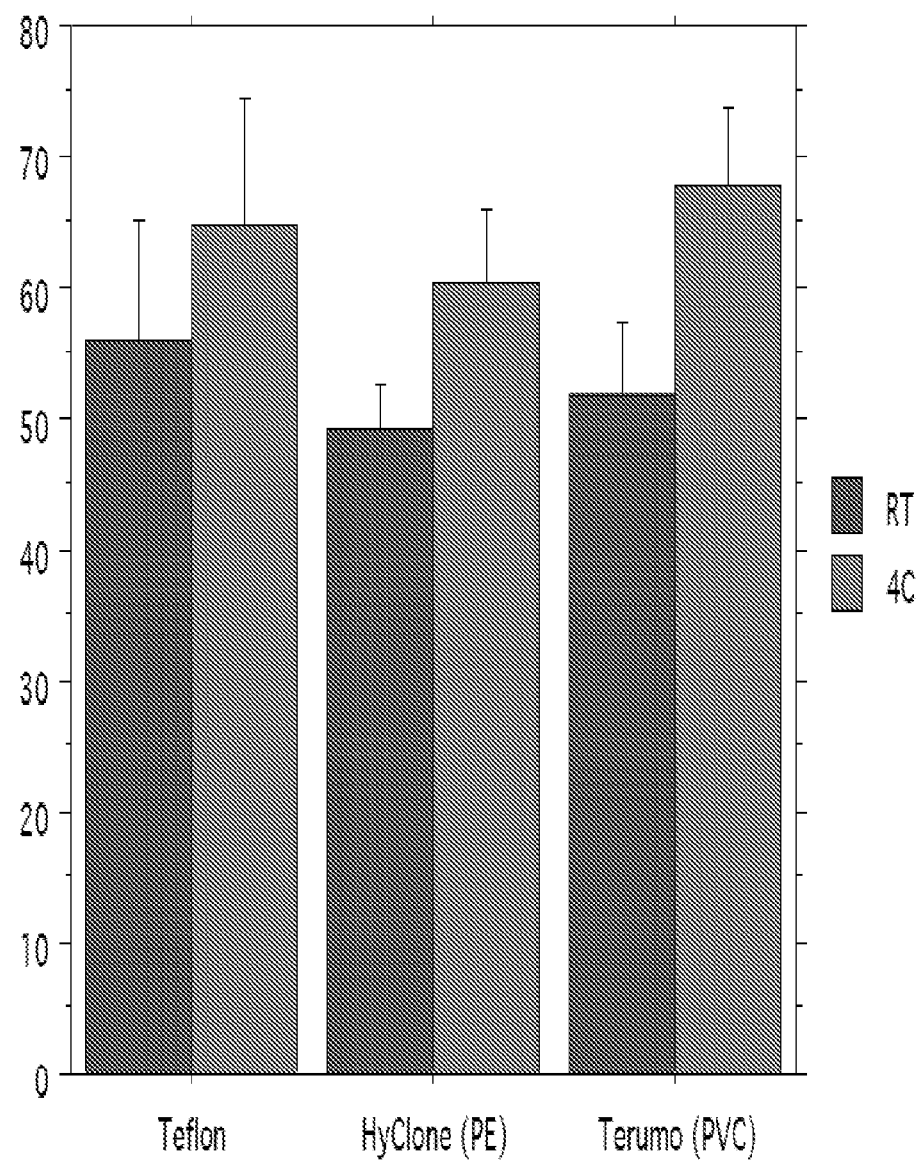
FIGS. 2A-E are a set of diagrams showing that, when stem cells were shipped in three types of bags over a period of 3 days, both bag types and shipping temperatures affected the recovery rate (FIG. 2A), cell viability (FIG. 2B), the level of $CD34^+$ cell population (FIG. 2C), the level of $CD133^+$ cell population (FIG. 2D), and CFUs (FIG. 2E) to different degrees.
Figure 2B:
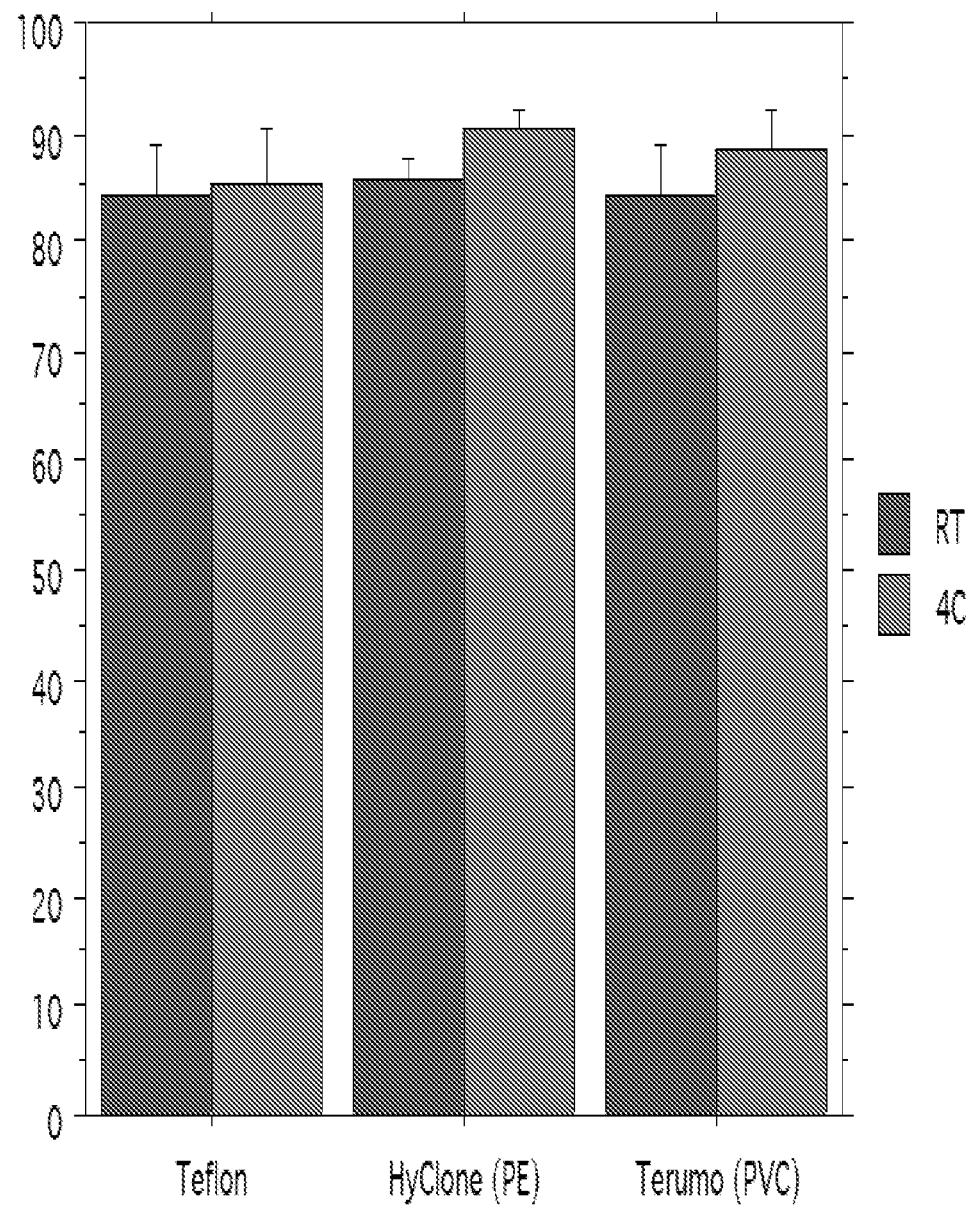
Figure 2C:
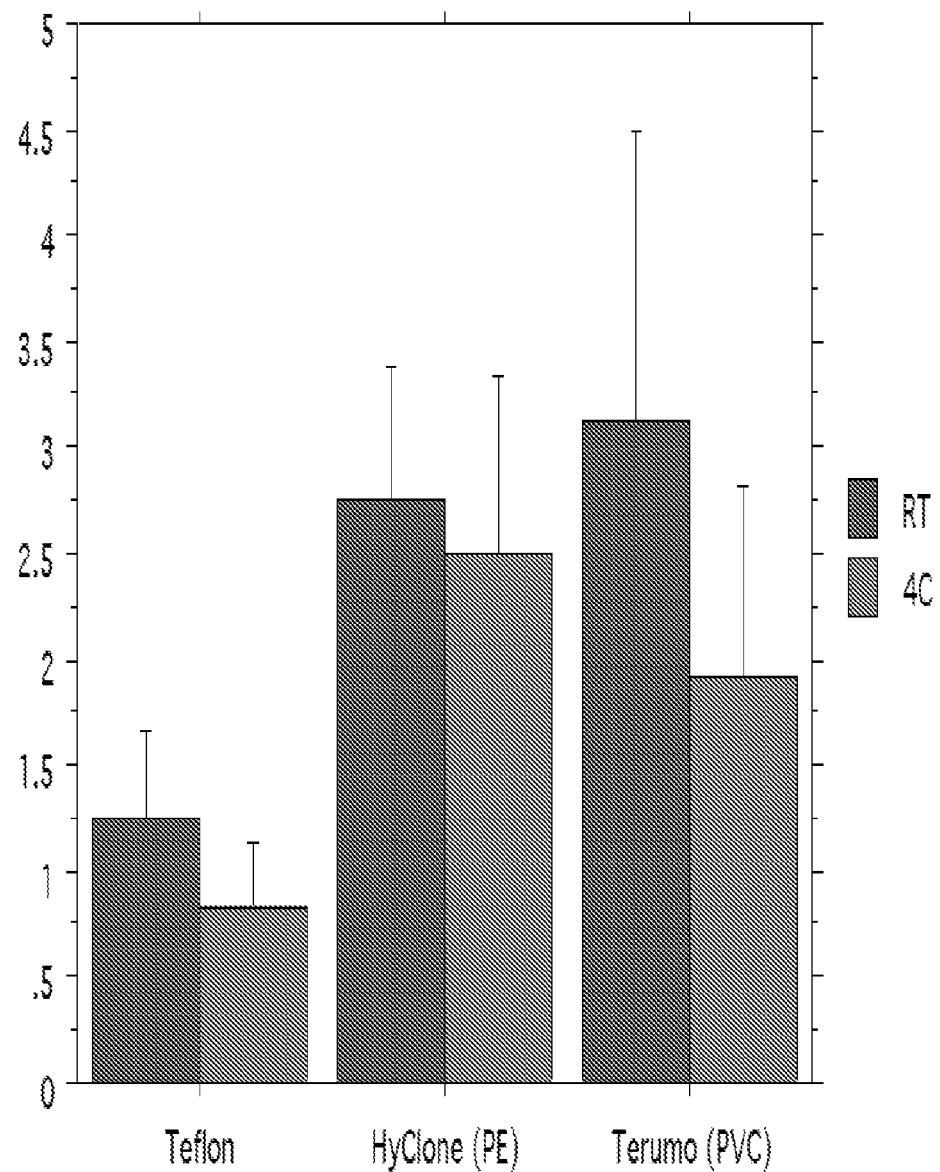
Figure 2D:
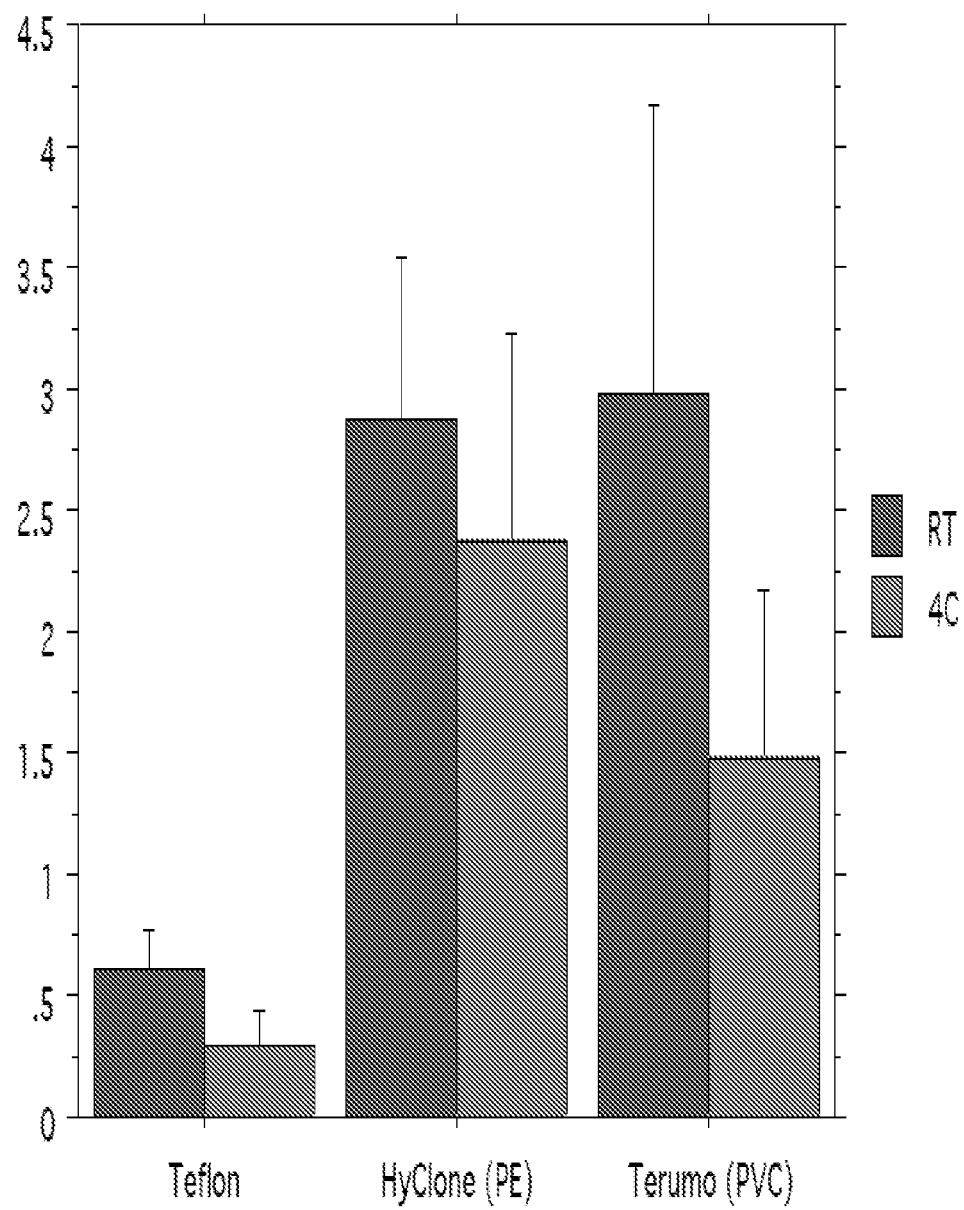
Figure 2E:
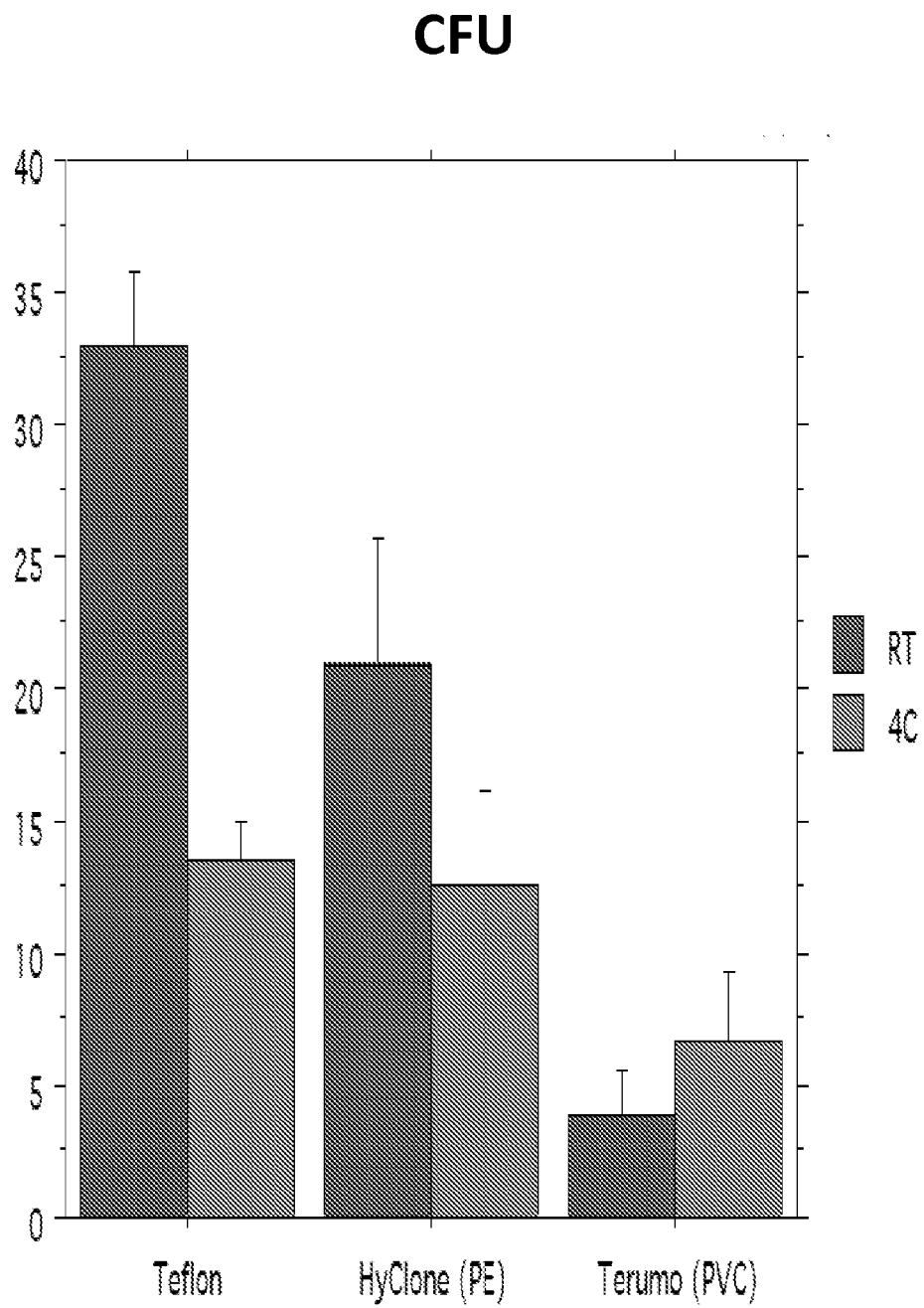

For example, while the recovery rates and cell viabilities were comparable among the three bag types (see FIGS. 2A and B), levels of CD 34+ cell population and $CD 133^+$ cell population were higher in those shipped with HYCLONE PE sample bags and TERUMO (PVC) bags (FIGS. 2C and D). In contrast, the cells shipped with TEFLON® Bags had a significantly higher CFU than that of cells shipped with HYCLONE PE sample bags, which had a significantly higher CFU than that of cells shipped with TERUMO (PVC) bags (FIG. 2E).

With regards to the shipping temperatures, cells shipped at RT show trends of lower recovery rates or cell viabilities (FIGS. 2A and B). However, it was unexpected that the cells shipped at RT had higher levels of $CD 34^+$ cell population and $CD 133^+$ cell population regardless of bag types (FIGS. 2C and D). Furthermore, it was also unexpected that cells shipped in the TEFLON® Bags at RT had the highest CFU level and that, similarly, cells shipped in the HYCLONE PE sample bags at RT also had a high CFU level.

The above results demonstrated that shipping stem cells at RT had unexpected higher levels of CFU or higher levels of CD 34+ cell population and $CD 133^+$ cell population.

2. Media

Figure 3:
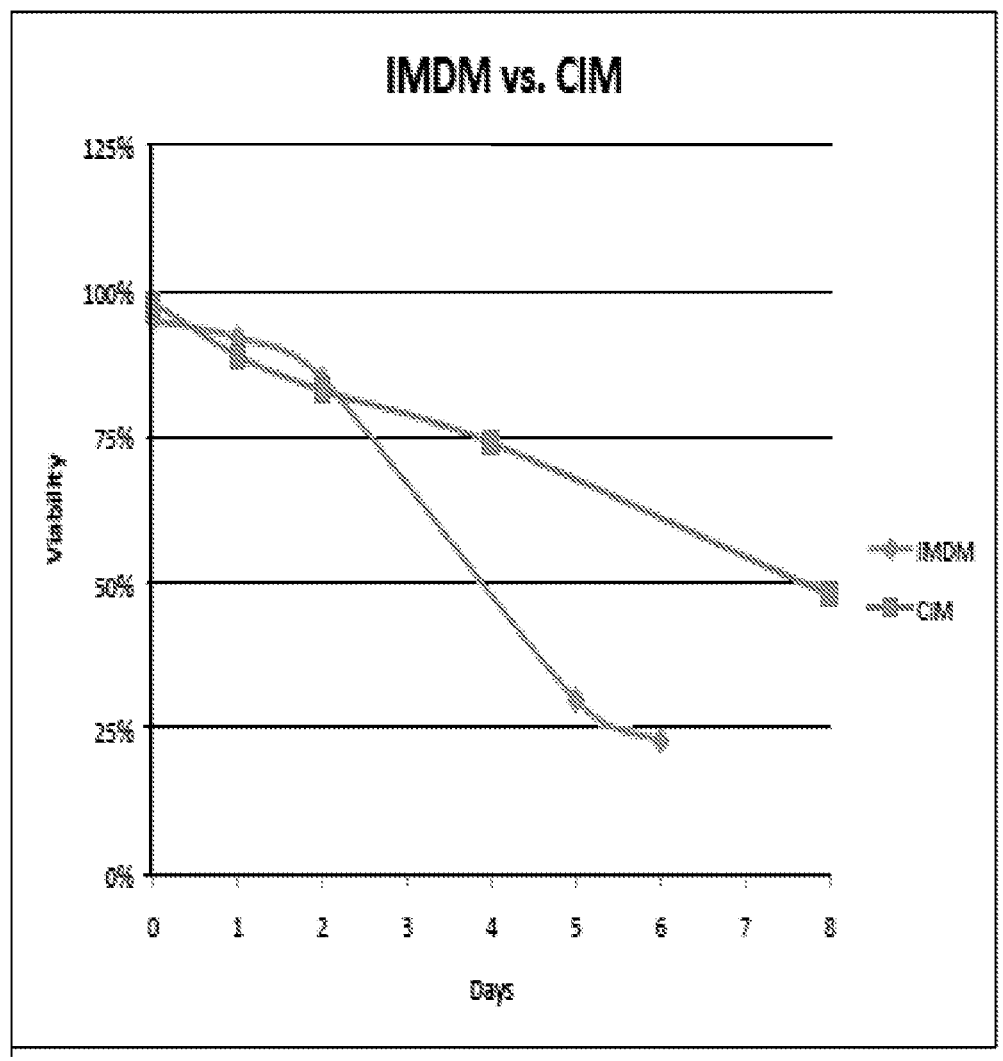
FIG. 3 is a table and a diagram showing effects of IMDM and CIM on cell viability at RT.
Figure 4:
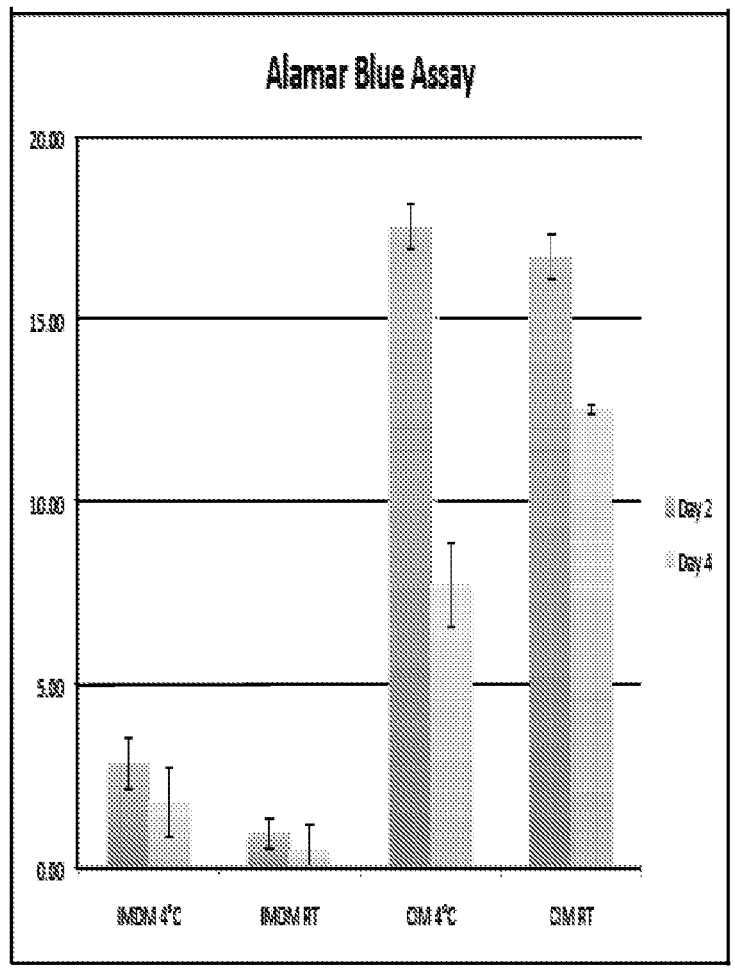
FIG. 4 is a table and a diagram showing effects of IMDM and CIM media on cell viability at RT and 4° C.

The effects of shipping media were also examined. If was found that cells shipped in the CIM medium had higher cell viability than those shipped in IMDM (FIGS. 3 and 4) after about 2 days. In particular, after 5 days, cells in the CIM medium still had a viability of about 74%.

Figure 5A:
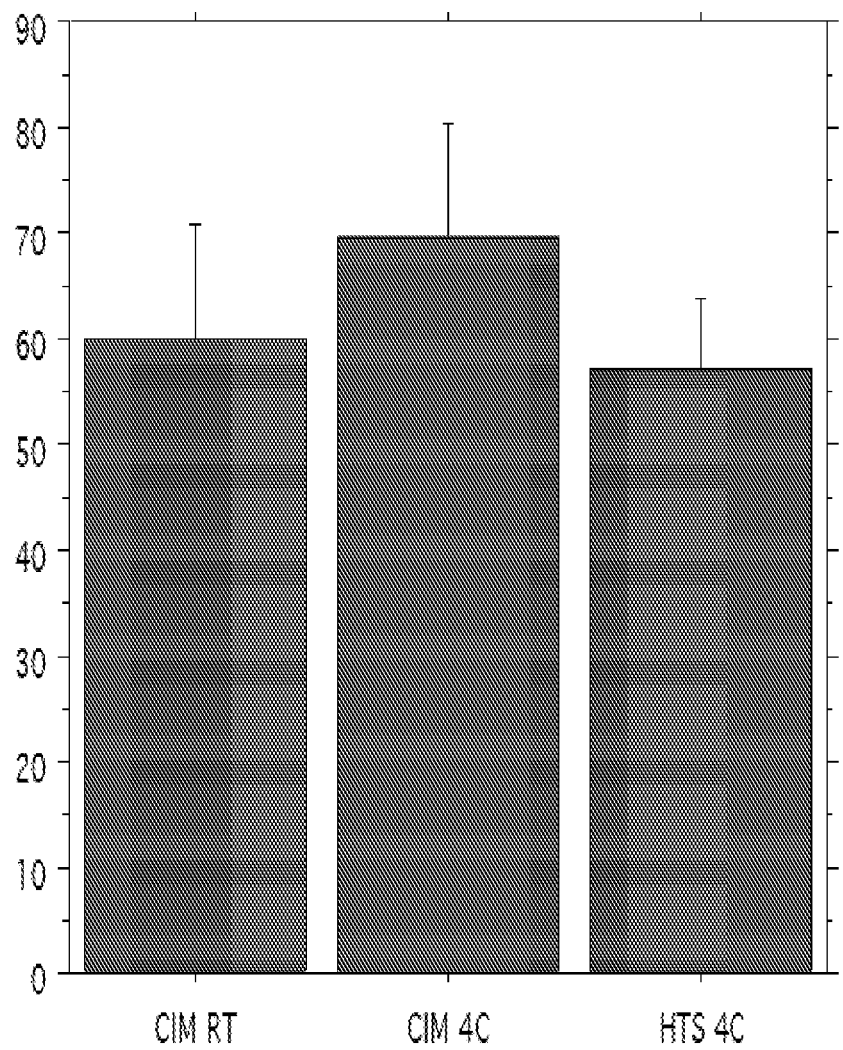
FIGS. 5A-E are a set of diagrams showing that, when cells were shipped in TEFLON bags at RT or 4° C., CIM and HTS media had different effects on cell recovery rates (5A), viabilities (5B), $CD34^+$ cell levels (5C), $CD123^+$ cell levels (5D), and CFUs (5E).
Figure 5B:
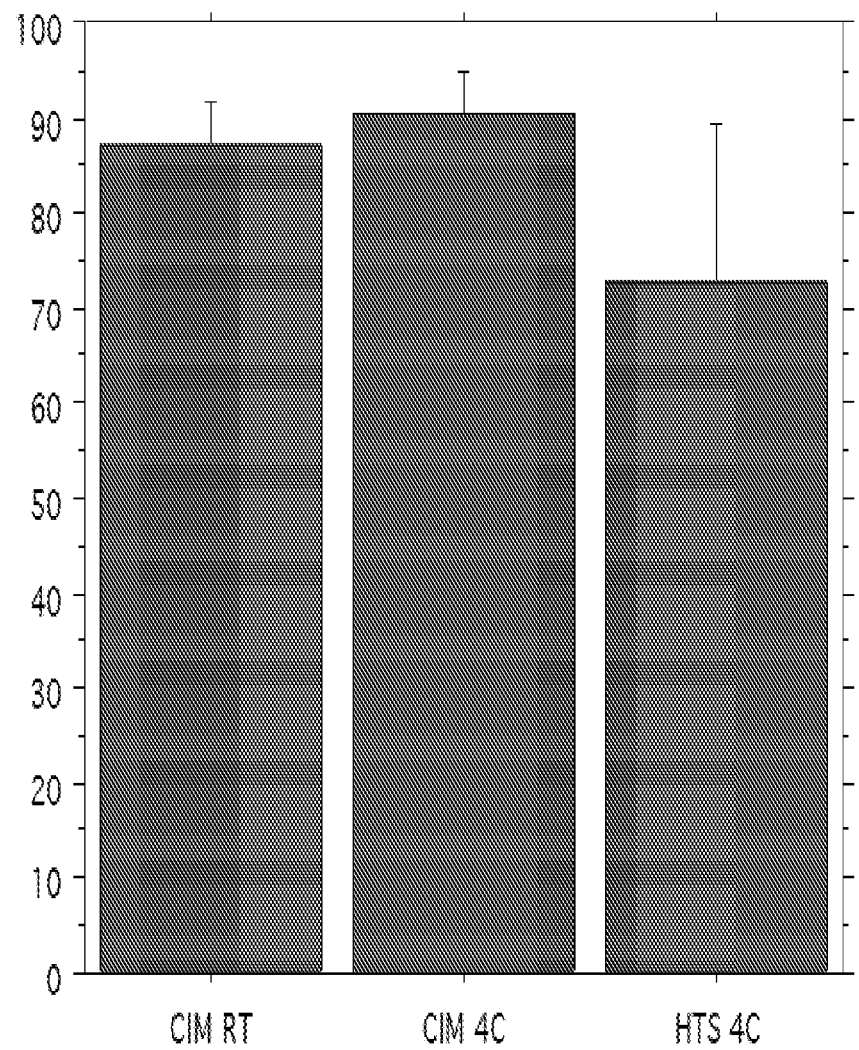
Figure 5C:
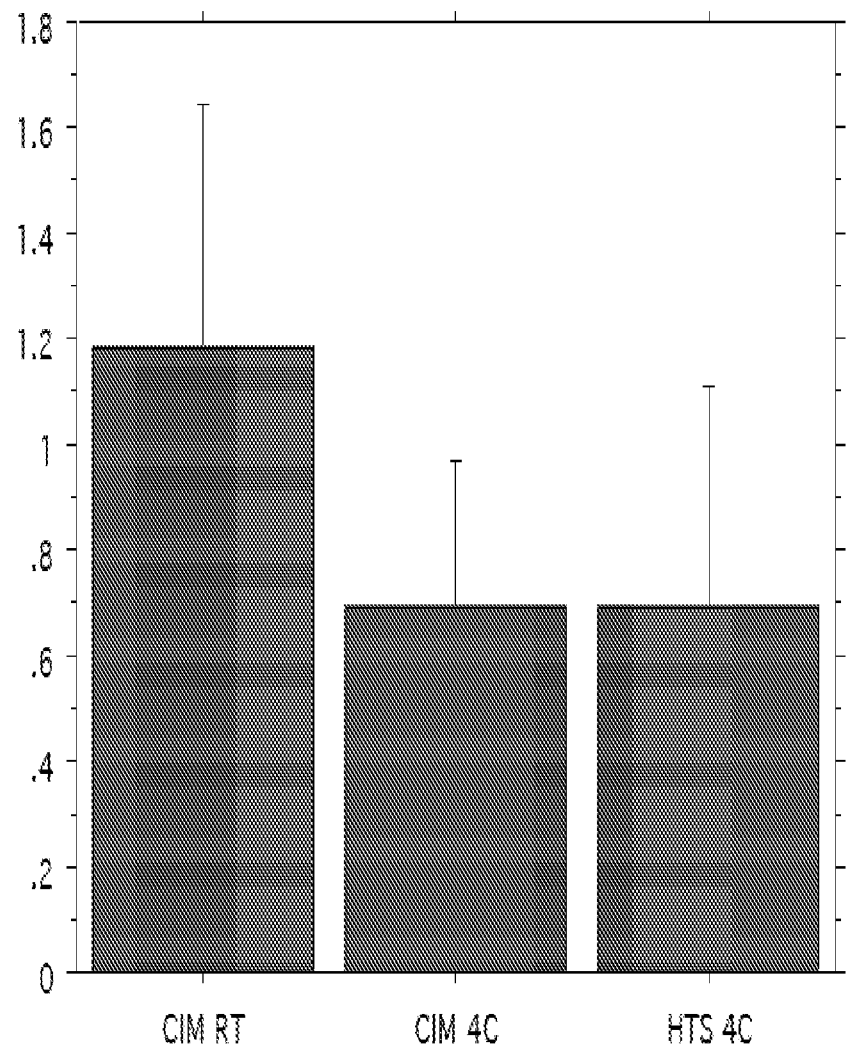
Figure 5D:
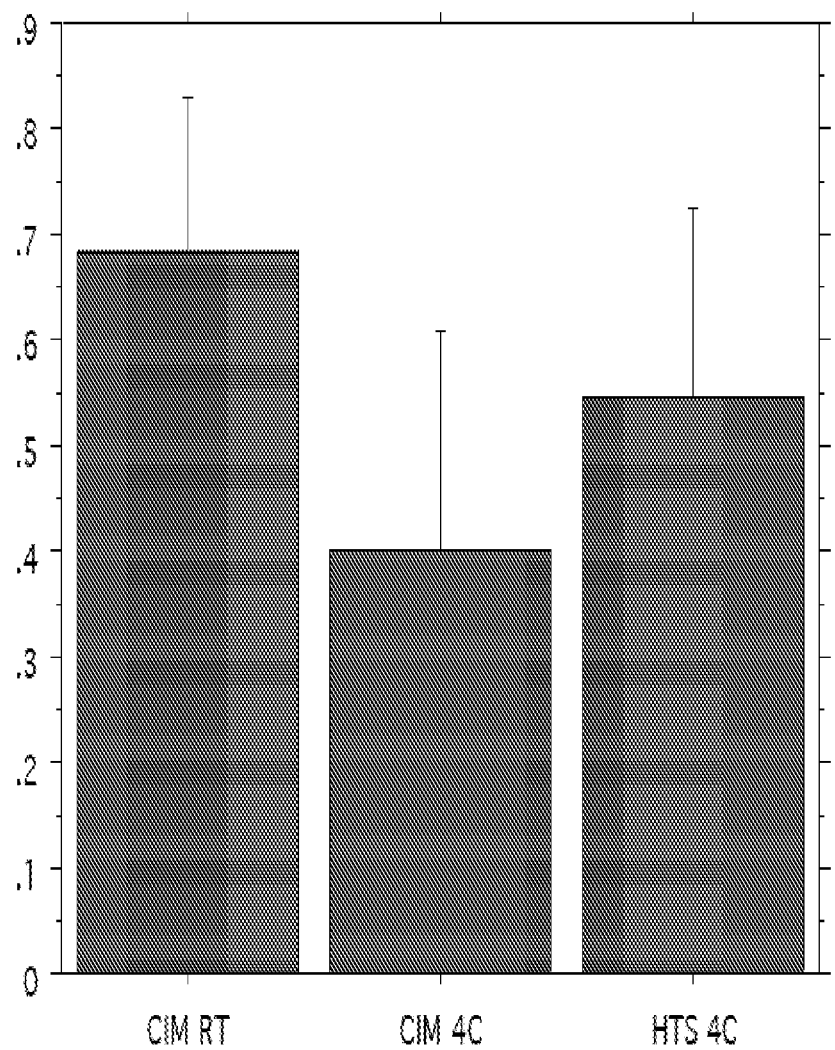
Figure 5E:
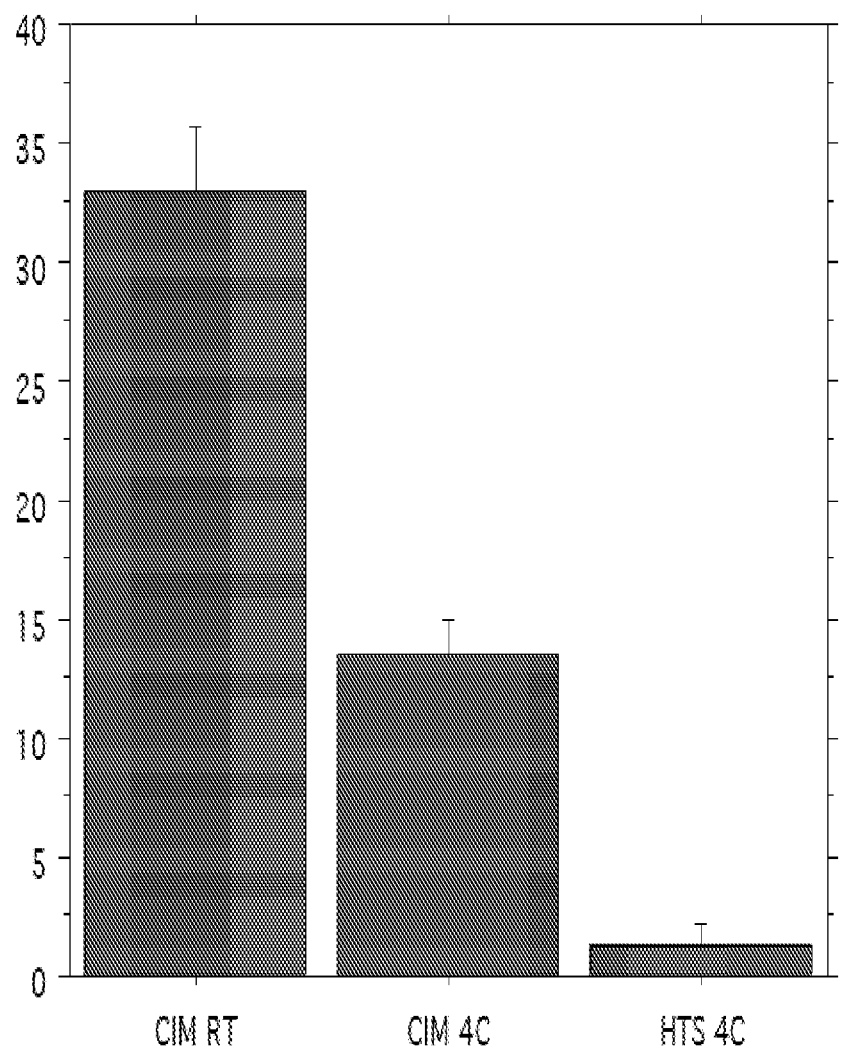

The CIM medium was then compared with a HYPOTHERMOSOL® (HTS) medium (BIOLIFE SOLUTIONS). It was found that, in general, cells shipped in the CIM medium in TEFLON bags at RT or 4° C. had cell recovery rates, viabilities, and $CD 34^+$ cell levels comparable to or higher than those in the HTS medium (FIGS. 5A-C). It was unexpected that cells shipped in the CIM medium at RT had the highest values for the $CD 34^+$ cell levels, the $CD 133^+$ cell levels, and CFU. It was also found that 1% NSA improved the cell viabilities in both HTS and CIM regardless of bag types. See tables 1-3 below.

TABLE 1

| | Shipping Condition | | | | | |
|---|---|---|---|---|---|---|
| | HTS 4° C. | | CIM RT | | CIM 4° C. | |
| | Medium for cell re-suspension | | | | | |
| | PBS | NSA | PBS | NSA | PBS | NSA |
| Viability | 67.3% | 94.0% | 50.0% | 87.0% | 68.7% | 96.0% |

Shiping Bag: Teflon

TABLE 2

| Shipping Bag | | | | | | | | |
|---|---|---|---|---|---|---|---|---|
| | Terumu | | | | HyClone | | | |
| | Transport condition | | | | | | | |
| | CIM RT | | CIM 4° C. | | CIM RT | | CIM 4° C. | |
| Medium for cell re-suspension | PBS | NSA | PBS | NSA | PBS | NSA | PBS | NSA |
| Viability | 14.0% | 83.0% | 28.5% | 87.5% | 16.5% | 75.5% | 10.5% | 80.0% |

TABLE 3

| Hour | 0 | 1 | 2 | 3 | 4 | 5 |
|---|---|---|---|---|---|---|
| Viability (Trypan blue exclusion) | 87.5% | 80.0% | 81.0% | 81.0% | 82.0% | 80.0% |
| Viability (7AAD) | 78.7% | 79.0% | 80.2% | 80.5% | 79.4% | 83.1% |

Cells are suspend in 1% NSA

In sum, it was found that, among the bags used for the testing of the procedures, the TEFLON bag gave the best CFU counts. However, as there was no GMP source of these bags and the TEFLON bags required open handling of the contents, extra care should be taken to avoid risk of contamination. The HYCLONE bags had higher viability, total nucleated counts, and CFU counts than TERUMO bags. Therefore, the HYCLONE bags were chosen for further shipping and experiments.

Addition assays were conduced to examine temperatures on cells shipped in CIM and the TEFLON bags. The data is shown below.

1. Human Mononuclear Cells in TEFLON bag, Incubation at 4° C./CO2 independent medium

| Assays | Day 0 Mon | Day 1 Tues | Day 2 Wed | Day 4 Fri | Day 7 Mon |
|---|---|---|---|---|---|
| FACS | | | | | |
| CD34 | 0.93% | 0.96% | 1.07% | 0.76 | 1.04% |
| CD133 | 0.64% | 0.89% | 0.58 | 0.6 | 0.59% |
| Cell Viability | | | | | |
| TrypanBlue negative | 94% | 92% | 90% | 82% | 86% |
| Total MNC number | $35 \times 10^6$ | $33 \times 10^6$ | $31 \times 10^6$ | $25 \times 10^6$ | $22 \times 10^6$ |

2. Human Mononuclear Cells in TEFLON bag, Incubation at 4° C./CO2 independent medium

| Assays | Day 0 Mon | Day 1 Tues | Day 2 Wed | Day 4 Fri | Day 7 Mon |
|---|---|---|---|---|---|
| FACS | | | | | |
| CD34+ | 0.88% | 0.68% | 0.80% | 0.73% | 0.95% |
| CD133+ | 0.99% | 1.02% | 0.79% | 0.60% | 0.67% |
| Cell Viability | | | | | |
| TrypanBlue negative | 94% | 90% | 87% | 77% | 84% |
| Total MNC number | $40 \times 10^6$ | $36 \times 10^6$ | $33 \times 10^6$ | $28 \times 10^6$ | $26 \times 10^6$ |

3. Human Mononuclear Cells in TEFLON bag, Incubation at RT/CO2 independent medium

| Assays | Day 0 Mon | Day 1 Tues | Day 2 Wed | Day 4 Fri | Day 8 Tue |
|---|---|---|---|---|---|
| FACS | | | | | |
| CD34 | 0.88% | 1.05% | 1.99% | 2.18% | 1.46% |
| CD133 | 0.92% | 1.18% | 2.20% | 2.19% | 1.42% |
| Cell Viability | | | | | |
| TrypanBlue negative | 98% | 89% | 83% | 74% | 48% |
| Total MNC number | $31 \times 10^6$ | $26 \times 10^6$ | $23 \times 10^6$ | $19 \times 10^6$ | $8.4 \times 10^6$ |

4. Human Mononuclear Cells in TEFLON bag, Incubation at 37° C./CO2 independent medium Unit P.22

| Assays | Day 0 Mon | Day 1 Tues | Day 2 Wed | Day 4 Fri | Day 7 Mon |
|---|---|---|---|---|---|
| FACS | | | | | |
| CD34+ | 0.88% | 0.56% | 0.55% | 0.65% | 0.62% |
| CD133 | 0.99% | 0.64% | 0.71% | 0.56% | 0.87% |
| Cell Viability | | | | | |
| TrypanBlue negative | 94% | 86% | 81% | 66% | 80% |
| Total MNC number | $40 \times 10^6$ | $20 \times 10^6$ | $17 \times 10^6$ | $14 \times 10^6$ | $6.4 \times 10^6$ |

As shown in the tables above, human mononuclear cells in the TEFLON bags incubation at RT in a $CO_2$ independent medium had the highest relative levels for $CD34^+$ cells or $CD133^+$ cells over the 8-day period.

The foregoing example and description of the preferred embodiments should be taken as illustrating, rather than as limiting the present invention as defined by the claims. All publications cited herein are hereby incorporated by reference in their entirety. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

What is claimed is:

1. A packaging product suitable for long distance shipping at a temperature within 5-40° C. over a period of at least 24 hours comprising
   a composition (i) containing hematopoietic stem cells and a $CO_2$ independent medium that contains serum and (ii) being substantially free of red blood cells, and
   a container comprising a substrate that comprises a polymer and holds the composition, wherein in the container is sealed, and
   wherein after shipping the packaging product at a temperature within the range of 5-40° C. over a period of at least 24 hours, the hematopoietic stem cells are capable of forming more than 2 $CFU/5\times10^4$ cells and wherein the polymer is polytetrafluoroethylene (PTFE), perfluoroalkoxy (PFA), fluorinated ethylene propylene (FEP), polyvinylidene fluoride (PVDF), polyethylene, or polyvinyl chloride (PVC).

2. The packaging product of claim 1, wherein the container is a bag, a tube, a syringe, or a vial for an injector.

3. The packaging product of claim 1, wherein the composition has a temperature within the range of 5-30° C.

4. The packaging product of claim 1, wherein the medium contains 0.5-20% serum.

5. The packaging product of claim 4, wherein the medium contains human serum.

6. The packaging product of claim 1, wherein the cells have been frozen and thawed.

7. The packaging product of claim 1, wherein the cells have not been frozen.

8. The packaging product of claim 1, wherein the cells are $CD34^+$ or $CD133^+$.

9. A method for making the packaging product of claim 1, comprising,
   providing a composition containing hematopoietic stem cells;
   providing a container comprising a substrate, wherein the substrate comprises a polymer; and
   placing the composition in the container; and, sealing the container, wherein the polymer is polytetrafluoroethylene (PTFE), perfluoroalkoxy (PFA), fluorinated ethylene propylene (FEP), polyvinylidene fluoride (PVDF), polyethylene, or polyvinyl chloride (PVC).

10. A method for shipping hematopoietic stem cells, comprising providing the packaging product of claim 1, and delivering the packaging product to a recipient, wherein the delivering step is conducted over at least 1 day while the composition of the packaging product has a temperature within the range of 5-30° C., wherein after delivering the pluripotent cells delivered are capable of forming more than 2 $CFU/5\times10^4$ cells.

11. The method of claim 10, wherein the delivering step is conducted at a temperature within the range of 10-30° C.

12. The method of claim 10, wherein, upon the delivering, the cells have a recovery rate of more than 40%.

13. The method of claim 10, wherein, upon the delivering, the cells have more than 0.5% $CD34^+$ cells.

14. The method of claim 10, wherein, upon the delivering, the cells have more than 0.25% $CD133^+$ cells.

15. The method of claim 10, wherein, upon the delivering, the cells are capable of forming more than 2 $CFU/5\times10^4$ cells.

16. The method of claim 10, wherein the delivering step is conducted over at least 2 days.

17. The packaging product of claim 1, wherein, after being kept at 5-40° C. for over 1-8 days, the cells have a recovery rate of more than 40% or a viability of more than 50%.

* * * * *